United States Patent
Xue et al.

(10) Patent No.: US 10,322,108 B2
(45) Date of Patent: Jun. 18, 2019

(54) N-BENZOATE GROUP SUBSTITUTED BENZOPYRROLINE-2-ONE DERIVATIVE AND USE THEREOF

(71) Applicant: BEIJING HANMI PHARMACEUTICAL CO., LTD., Beijing (CN)

(72) Inventors: Hai Xue, Beijing (CN); Tao Zhao, Beijing (CN); Mi Young Cha, Beijing (CN); Maengsup Kim, Beijing (CN)

(73) Assignee: Beijing Hanmi Pharmaceutical Co., Ltd., Beijing (CN)

( * ) Notice: Subject to any disclaimer, the term of this patent is extended or adjusted under 35 U.S.C. 154(b) by 0 days.

(21) Appl. No.: 15/541,137

(22) PCT Filed: Jan. 22, 2016

(86) PCT No.: PCT/CN2016/071778
§ 371 (c)(1),
(2) Date: Jun. 30, 2017

(87) PCT Pub. No.: WO2016/119641
PCT Pub. Date: Aug. 4, 2016

(65) Prior Publication Data
US 2017/0368028 A1   Dec. 28, 2017

(30) Foreign Application Priority Data

Jan. 28, 2015  (CN) .......................... 2015 1 0043379

(51) Int. Cl.
| | |
|---|---|
| *A61K 31/404* | (2006.01) |
| *C07D 209/10* | (2006.01) |
| *C07D 209/08* | (2006.01) |
| *A61K 31/03* | (2006.01) |
| *A61K 31/192* | (2006.01) |
| *A61K 31/196* | (2006.01) |

(52) U.S. Cl.
CPC ............ *A61K 31/404* (2013.01); *A61K 31/03* (2013.01); *A61K 31/192* (2013.01); *A61K 31/196* (2013.01); *C07D 209/08* (2013.01); *C07D 209/10* (2013.01); *Y02A 50/409* (2018.01)

(58) Field of Classification Search
CPC .. A61K 31/404; A61K 31/196; A61K 31/192; A61K 31/03; C07D 209/10; C07D 209/08
See application file for complete search history.

(56) References Cited

U.S. PATENT DOCUMENTS

| 5,382,593 A | 1/1995 | Le Baut et al. |
| 2002/0028936 A1 | 3/2002 | Sperl et al. |
| 2014/0038941 A1 | 2/2014 | Sawada et al. |

FOREIGN PATENT DOCUMENTS

| EP | 2759533 A1 | 7/2014 |
| JP | 06179652 A | 6/1994 |
| JP | 2004505005 A | 2/2004 |
| JP | 2011001301 A | * 1/2011 |
| JP | 2011001309 A | 1/2011 |
| WO | 2013042782 A1 | 3/2013 |
| WO | 2014026328 A1 | 2/2014 |

OTHER PUBLICATIONS

Banker, Gilbert. Modern Pharmaceutics 3rd ed. Marcel Dekker, Inc. New York, 1996.*
RN: 1349823-64-8 (Entered STN : Dec. 6, 2011), CN: 2H-Indol-2-one, 1-[4-amino-7-(1-methylethyl)-7H-pyrrolo[2,3-d] pyrimidin-5-yl]-1,3-dihydro-3-(phenylmethylene)-, (3E)- (CA Index Name), Retrieved from STN, <<URL:https://stnweb-japan.cas.org/>>.
European Search Report dated Jun. 18, 2018 for EP Application No. 16742703.8.

* cited by examiner

*Primary Examiner* — Emily A Bernhardt
*Assistant Examiner* — Laura M Daniel
(74) *Attorney, Agent, or Firm* — Fox Rothschild LLP

(57) ABSTRACT

Disclosed are a compound, a stereisomer and a tautomer thereof, a pharmaceutically acceptable salt thereof, and a solvate or a prodrug thereof, which can be used for preventing or treating a RORγ mediated disease. The compound has the structural formula (I).

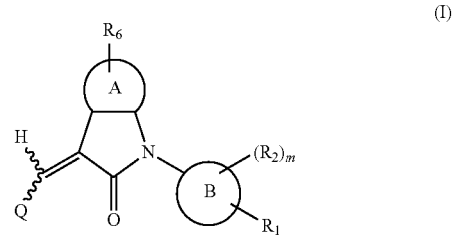

14 Claims, 1 Drawing Sheet

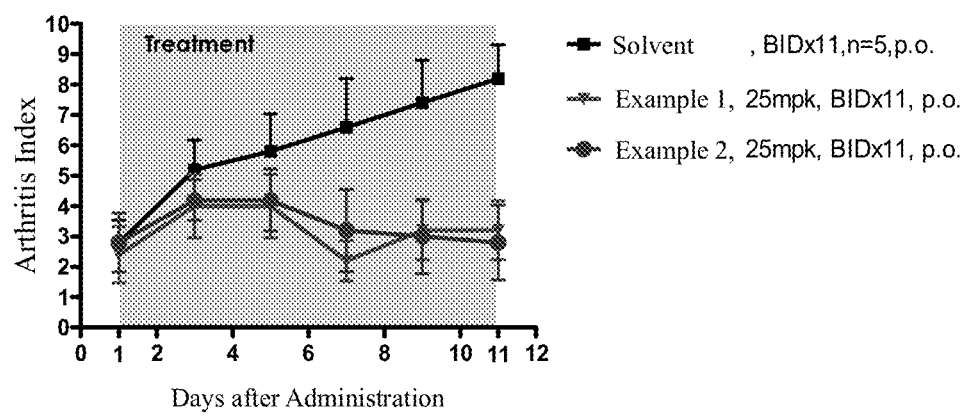

N-BENZOATE GROUP SUBSTITUTED BENZOPYRROLINE-2-ONE DERIVATIVE AND USE THEREOF

TECHNICAL FIELD

The present application relates to compounds that can be used as modulators of retinoid-related orphan receptor γ (RORγ), pharmaceutical compositions thereof, use thereof in manufacturing pharmaceuticals and method for treating and/or preventing RORγ-mediated diseases in mammals (especially humans) using the same.

BACKGROUND ART

Nuclear receptors are a class of ligand-dependent transcription factor superfamily, which are widely distributed in organisms, and play a role in aspects such as metabolism, development, biorhythm, inflammation, immune regulation and the like. The ligands for nuclear receptors include thyroid hormones, steroid hormones, retinoic acids, fatty acids, sterols and the like. In addition, there is a class of nuclear receptors for which the ligands have not been determined so far, and these receptors are called orphan nuclear receptors. Retinoid-related orphan receptors (RORs), also known as NF1R, are named due to their similarity to retinoic acid receptor (RAR) and retinoid X receptor (RXR) in their gene sequences. ROR subfamily mainly includes three members, RORα, RORβ and RORγ. At present, relatively more research is being conducted on RORα and RORγ and ligands thereof (modulators). RORα is widely expressed in various tissues and organs in the body. It may exist in brain, kidney, liver, testis, ovary, skeletal muscle, thymus, skin, lung and adipose tissue, wherein the highest expression level exists in brain tissue, especially cerebellar and thalamus. Recent researches also show that RORα participates in the activity of osteoblast of human body by stimulating osteoblast-promoting factors and inhibiting inflammatory reactions. RORγ mainly includes two subtypes, RORγ1 and RORγt (RORγ2), in which RORγ1 is distributed in skeletal muscle, thymus, testis, pancreas, prostate, heart, liver, etc.; while RORγt is only expressed in immune cells and is an RORγ subtype which is specific for T cells. Th17 cells are a class of Th cell subgroup which were recently proved to be capable of specifically producing cytokine IL-17. They participate in inducing autoimmune diseases, have strong pro-inflammatory effects, and are relevant to the occurrence and development of various autoimmune diseases, such as multiple sclerosis, psoriasis, arthritis, asthma, and the like. RORγ is a key driving factor of the differentiation and regulation of TH17 cells, and therefore gradually becomes an emerging potential target for developing drugs for autoimmune diseases. ROR inverse agonist (antagonist) blocks the occurrence and development of inflammation by affecting the functions of RORγ, regulating the proliferation and growth of TH17 cells, and inhibiting the generation of cytokine IL-17. In recent years, there have been a number of research articles showing that such an important physiological function of RORγ has been verified in experiments of in vitro inhibition of the generation of cytokine IL-17 and in mouse autoimmune disease models (CIA model, EAE model, etc.). (*Nature* 2011, 472, 486-490; *Nature* 2011, 472, 491-496; *ACS Chem. Biol.* 2012, 7, 672-677; *Bioorg. Med. Chem. Lett.* 23 (2013) 532-536; *Journal Exp Med.* 2008; 205(5):1063-1075; *Immunol Res.* 2001; 23(2-3):99-109; *Cell* 126, 1121-1133, Sep. 22, 2006; WO2012158784; WO2012100732; U.S. Pat. No. 8,389,739B1; WO2013160418; WO2013092939; WO2013169704; WO2013178362; *ACS Med. Chem. Lett.*, 2014, 5(1), 65-68; *Bioorg. Med. Chem.* 2014(22), 692-702; *J Immunol* 2014 (192), 2564-2575; *Immunity* 2014 (40), 477-489).

Since RORγ plays an important role in the occurrence and development of various autoimmune diseases, the synthesis of a series of novel compounds to regulate the function of RORγ is of great importance. This can lay a foundation for the treatment of autoimmune diseases.

SUMMARY OF THE INVENTION

The present application provides a series of compounds that can be used as modulators of retinoid-related orphan receptor γ (RORγ), pharmaceutical compositions thereof, use thereof in manufacturing pharmaceuticals and method for treating and/or preventing RORγ-mediated diseases in mammals (especially humans) using the same.

One aspect of the present application provides a compound, or a stereoisomer, a tautomer, a pharmaceutically acceptable salt, a solvate or a prodrug thereof, the compound having a structural formula (I):

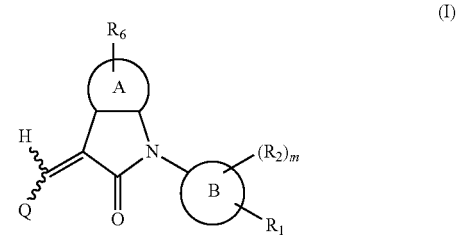

wherein,

A is 5- or 6-membered aryl or heteroaryl;

$R_6$ is selected from one or more of the following groups: alkyl, cycloalkyl, alkoxy, aryl, halogen, trifluoromethyl, amino, cyano, hydroxyl, carboxyl, halogenated alkyl, halogenated alkoxy, alkylamino, dialkylamino, alkylsulfonyl, aminosulfonyl, sulfonamido, amido, carbonyl, alkylaminocarbonyl and dialkylaminocarbonyl;

B is aryl or heteroaryl;

Q is aryl or heteroaryl, which is optionally and independently substituted by one or more of the following groups: halogen, trifluoromethyl, alkyl, cycloalkyl, alkoxy, hydroxyl, amino, cyano, nitro, carbonyl, aryl, heteroaryl, alkylamino, dialkylamino, alkylaminocarbonyl, dialkylaminocarbonyl, alkylsulfonyl and alkylcarbonyl, wherein the alkyl, cycloalkyl, alkoxy, aryl or heteroaryl group may be optionally substituted by one or more halogens;

$R_1$ is optionally and independently selected from the group consisting of —C(=O)OH, alkyl-OC(=O)—, amido, 5-tetrazole, HOC(CF$_3$)$_2$, phosphoric acid group, phosphate ester group, cyano, hydroxyl, amino, alkoxy, alkylaminocarbonyl, aminosulfonyl, sulfonamido and alkylsulfonyl;

$R_2$ is hydrogen, hydroxyl, halogen, cyano, nitro, (C$_{1-4}$) alkyl, (C$_{1-4}$)alkoxy or (C$_{1-3}$)alkylC(=O)O—, wherein the (C$_{1-4}$)alkyl or (C$_{1-4}$)alkoxy group may be optionally substituted by one or more halogens;

m is 0, 1, 2, 3 or 4; and the heterocyclyl or heteroaryl group has one or more heteroatoms selected from the group consisting of N, O and S.

According to some embodiments, some compounds of the present application have a structural formula (Ia):

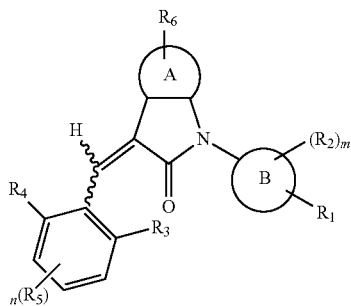

(Ia)

wherein,

A is 5- or 6-membered aryl or heteroaryl;

$R_6$ is selected from one or more of the following groups: alkyl, cycloalkyl, alkoxy, aryl, halogen, trifluoromethyl, amino, cyano, carboxyl, halogenated alkyl, halogenated alkoxy, alkylamino, dialkylamino, alkylsulfonyl, aminosulfonyl, sulfonamide, amido, carbonyl, alkylaminocarbonyl and dialkylaminocarbonyl;

B is aryl or heteroaryl;

$R_1$ is optionally independently selected from the group consisting of —C(=O)OH, alkyl-OC(=O)—, amido, 5-tetrazole, HOC(CF$_3$)$_2$, phosphoric acid group, phosphate ester group, cyano, hydroxyl, amino, alkoxy, alkylaminocarbonyl, aminosulfonyl, sulfonamide and alkylsulfonyl;

$R_2$ is hydrogen, hydroxyl, halogen, cyano, nitro, (C$_{1-4}$)alkyl, (C$_{1-4}$)alkoxy or (C$_{1-3}$)alkylC(=O)O—, wherein the (C$_{1-4}$)alkyl or (C$_{1-4}$)alkoxy group may be optionally substituted by one or more halogens;

$R_3$, $R_4$, $R_5$ may be optionally independently selected from the group consisting of H, halogen, trifluoromethyl, alkyl, cycloalkyl, alkoxy, hydroxyl, amino, cyano, aryl, heteroaryl, alkylamino, dialkylamino, alkylsulfonyl and alkylcarbonyl;

m is 0, 1, 2, 3 or 4;

n is 0, 1, 2 or 3; and the heterocyclyl or heteroaryl has one or more heteroatoms selected from the group consisting of N, O and S.

According to some embodiments, some compounds of the present application have a structural formula (Ib):

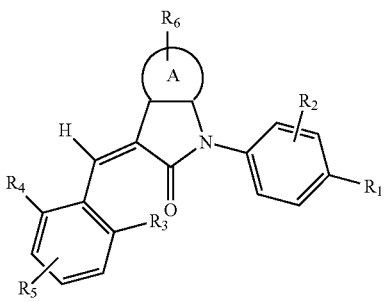

(Ib)

wherein,

A is phenyl, pyridyl, thienyl, furanyl or pyrimidyl;

$R_6$ is selected from one or more of the following groups: alkyl, cycloalkyl, alkoxy, aryl, halogen, trifluoromethyl, amino, cyano, carboxyl, halogenated alkyl, halogenated alkoxy, alkylamino, dialkylamino, alkylsulfonyl, aminosulfonyl, sulfonamide, amido, carbonyl, alkylaminocarbonyl and dialkylaminocarbonyl;

$R_1$ is optionally independently selected from the group consisting of —C(=O)OH, alkyl-OC(=O)—, amido, 5-tetrazole, HOC(CF$_3$)$_2$, phosphoric acid group, phosphate ester group, cyano, hydroxyl, amino, alkoxy, alkylaminocarbonyl, aminosulfonyl, sulfonamide and alkylsulfonyl;

$R_2$ is hydrogen, hydroxyl, halogen, cyano, nitro, (C$_{1-4}$)alkyl or (C$_{1-4}$)alkoxy or (C$_{1-3}$)alkylC(=O)O—, wherein the (C$_{1-4}$)alkyl or (C$_{1-4}$)alkoxy group may be optionally substituted by one or more halogens;

$R_3$, $R_4$, $R_5$ may be optionally independently selected from the group consisting of H, halogen, trifluoromethyl, alkyl, cycloalkyl, alkoxy, hydroxyl, amino, cyano, aryl, heteroaryl, alkylamino, dialkylamino, alkylsulfonyl and alkylcarbonyl;

m is 0, 1, 2, 3 or 4;

n is 0, 1, 2 or 3; and the heterocyclyl or heteroaryl has one or more heteroatoms selected from the group consisting of N, O and S.

According to some embodiments, some compounds of the present application have a structural formula (Ic):

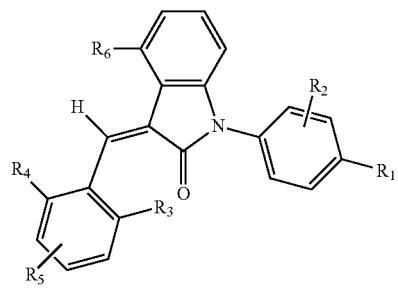

wherein, $R_1$ is optionally and independently selected from the group consisting of —C(=O)OH, alkyl-OC(=O)—, amido (e.g. —C(=O)NH$_2$, —C(=O)NHR, —C(=O)NRR$^a$, wherein R and R$^a$ both are selected from C$_{1-6}$ alkyl), 5-tetrazole, HOC(CF$_3$)$_2$, phosphoric acid group, phosphate ester group, cyano, hydroxyl, amino, alkoxy, alkylaminocarbonyl, aminosulfonyl, sulfonamido and alkylsulfonyl;

$R_2$ is hydrogen, hydroxyl, halogen, cyano, nitro, (C$_{1-4}$)alkyl, (C$_{1-4}$)alkoxy or (C$_{1-4}$)alkylC(=O)O— (e.g. (C$_{1-3}$)alkylC(=O)O—), wherein the (C$_{1-4}$)alkyl or (C$_{1-4}$)alkoxy group may be optionally substituted by one or more halogens;

$R_3$, $R_4$ and $R_5$ may be optionally and independently selected from the group consisting of H, halogen, trifluoromethyl, alkyl, cycloalkyl, alkoxy, hydroxyl, amino, cyano, aryl, heteroaryl, alkylamino, dialkylamino, alkylsulfonyl and alkylcarbonyl;

$R_6$ is selected from one or more of the following groups: alkyl, cycloalkyl, alkoxy, aryl, halogen, trifluoromethyl, amino, cyano, carboxyl, halogenated alkyl, halogenated alkoxy, alkylamino, dialkylamino, alkylsulfonyl, aminosulfonyl, sulfonamide, amido, carbonyl, alkylaminocarbonyl and dialkylaminocarbonyl; and the heterocyclyl or heteroaryl has one or more heteroatoms selected from the group consisting of N, O and S.

According to some embodiments, in formulas (I) and (Ia), (Ib), (Ic), m is 0 or 1, and when m is 1, $R_2$ is hydroxyl.

According to some embodiments, in formulas (I) and (Ia), (Ib), (Ic), $R_1$ is —C(=O)OH.

According to some embodiments, in formulas (I) and (Ia), (Ib), (Ic), $R_6$ is $C_{1-4}$ alkyl, cycloalkyl or alkoxy.

According to some embodiments, the compounds of the present application are represented by a formula (Id):

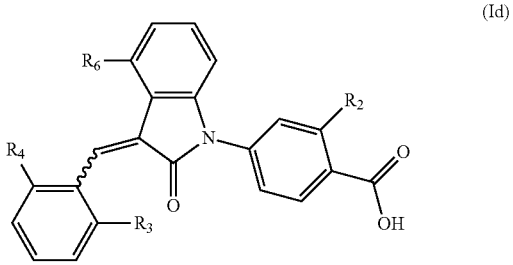

(Id)

wherein, $R_2$ is optionally selected from the group consisting of hydrogen, hydroxyl, halogen, amino, $(C_{1-4})$alkyl, $(C_{1-4})$alkoxy and $(C_{1-4})$alkylC(=O)O— (e.g. $(C_{1-3})$alkylC(=O)O—), wherein the $(C_{1-4})$alkyl or $(C_{1-4})$alkoxy group may be optionally substituted by one or more halogen atoms;

$R_6$ is selected from the following groups: hydrogen, halogen, trifluoromethyl, $(C_{1-4})$alkyl, $(C_{1-4})$alkoxy, $(C_{3-4})$cycloalkyl and $C_{5-10}$ aryl; and $R_3$ and $R_4$ are optionally independently selected from the group consisting of halogen (e.g. chlorine), trifluoromethyl, $(C_{1-4})$alkyl, $(C_{1-4})$alkoxy and $(C_{3-4})$cycloalkyl (e.g. cyclopropyl).

According to a further embodiment, in formula (Id), $R_2$ is optionally selected from the group consisting of hydrogen, hydroxyl, halogen, amino, $(C_{1-4})$alkoxy and $(C_{1-4})$alkylC(=O)O—, wherein the $(C_{1-4})$alkyl or $(C_{1-4})$alkoxy group may be optionally substituted by one or more halogen atoms; $R_6$ is selected from the following groups: hydrogen, halogen, trifluoromethyl, $(C_{1-4})$alkyl, $(C_{1-4})$alkoxy, $(C_{3-4})$cycloalkyl and $C_{5-10}$ aryl; $R_3$ is halogen; and $R_4$ is optionally independently selected from the group consisting of halogen, trifluoromethyl, $(C_{1-4})$alkyl, $(C_{1-4})$alkoxy and $(C_{3-4})$cycloalkyl.

According to a further embodiment, in formula (Id), $R_2$ is hydrogen, hydroxyl or halogen; $R_6$ is fluoro, methyl, trifluoromethyl or methoxy; $R_3$ is halogen (e.g. chlorine); and $R_4$ is optionally independently selected from the group consisting of halogen (e.g. chlorine), trifluoromethyl, $(C_{1-4})$alkyl, $(C_{1-4})$alkoxy and $(C_{3-4})$cycloalkyl (e.g. cyclopropyl).

According to a further embodiment, in formula (Id), $R_2$ is hydroxyl; $R_6$ is fluoro, methyl or methoxy; $R_3$ is halogen (e.g. chlorine); and $R_4$ is optionally independently selected from the group consisting of halogen (e.g. chlorine), trifluoromethyl, $(C_{1-4})$alkyl, $(C_{1-4})$alkoxy and $(C_{3-4})$cycloalkyl (e.g. cyclopropyl).

According to a further embodiment, in formula (Id), $R_2$ is hydroxyl; $R_6$ is methyl; $R_3$ is chloro; and $R_4$ is cyclopropyl, trifluoromethyl or chloro.

Another aspect of the present application relates to a pharmaceutical composition, which comprises one or more compounds of the present application, or a stereoisomer, a tautomer, a pharmaceutically acceptable salt, a solvate or a prodrug thereof, as well as a pharmaceutically acceptable excipient.

Yet another aspect of the present application relates to a pharmaceutical composition, which comprises one or more compounds of the present application, or a stereoisomer, a tautomer, a pharmaceutically acceptable salt, a solvate or a prodrug thereof; as well as one or more anti-inflammatory drugs selected from the group consisting of non-steroidal anti-inflammatory drugs (NSAIDs), non-specific and specific cyclooxygenase-2 inhibitors, gold compounds, corticosteroids, tumor necrosis factor receptor antagonists, salicylate esters or salts, immunosuppressants and methotrexate; as well as a pharmaceutically acceptable excipient.

Another aspect of the present application relates to a compound of the present application, or a stereoisomer, a tautomer, a pharmaceutically acceptable salt, a solvate or a prodrug thereof, for regulating the activity of RORγ (e.g. inhibiting the activity of RORγ), or for preventing or treating RORγ-mediated diseases.

Another aspect of the present application relates to use of a compound of the present application, or a stereoisomer, a tautomer, a pharmaceutically acceptable salt, a solvate or a prodrug thereof, in manufacturing a medicament for regulating the activity of RORγ (e.g. inhibiting the activity of RORγ).

Another aspect of the present application relates to use of a compound of the present application, or a stereoisomer, a tautomer, a pharmaceutically acceptable salt, a solvate or a prodrug thereof, in manufacturing a medicament as an RORγ modulator (e.g. an inhibitor of the activity of RORγ).

Another aspect of the present application relates to a compound of the present application, or a stereoisomer, a tautomer, a pharmaceutically acceptable salt, a solvate or a prodrug thereof, for regulating the activity of RORγ (e.g. inhibiting the activity of RORγ).

Another aspect of the present application relates to a compound of the present application, or a stereoisomer, a tautomer, a pharmaceutically acceptable salt, a solvate or a prodrug thereof, for preventing or treating an RORγ-mediated disease.

Another aspect of the present application relates to a method for regulating RORγ, which comprises contacting a compound of the present application, or a stereoisomer, a tautomer, a pharmaceutically acceptable salt, a solvate or a prodrug thereof, with RORγ.

Another aspect of the present application relates to a method for preventing or treating an RORγ-mediated disease, comprising administrating a preventively or therapeutically effective amount of a compound of the present application, or a stereoisomer, a tautomer, a pharmaceutically acceptable salt, a solvate or a prodrug thereof, or a pharmaceutical composition of the present application, to a subject in need thereof. Another aspect of the present application relates to a method for preventing or treating an RORγ-mediated disease, comprising administrating a preventively or therapeutically effective amount of a compound of the present application, or a stereoisomer, a tautomer, a pharmaceutically acceptable salt, a solvate or a prodrug thereof, as well as one or more anti-inflammatory drugs including, but not limited to, one or more anti-inflammatory drugs selected from the group consisting of non-steroidal anti-inflammatory drugs (NSAIDs), non-specific and specific cyclooxygenase-2 inhibitors, gold compounds, corticosteroids, tumor necrosis factor receptor antagonists, salicylate esters or salts, immunosuppressants and methotrexate, to a subject in need thereof.

According to some embodiments, the RORγ-mediated disease described in the present application may be an autoimmune disease and/or an inflammatory disease.

According to some embodiments, the RORγ mediated disease to be prevented or treated is selected from the group consisting of multiple sclerosis, rheumatoid arthritis, psoriasis, crohn's disease, asthma, systemic lupus erythematosus, chronic obstructive pulmonary disease, rejections of tissue graft and of transplanted organ, scleroderma, purpura, autoimmune hemolytic and thrombocytopenia symptoms, irritable bowel syndrome, osteoarthritis, kawasaki disease, hashimoto thyroiditis, mucosal leishmaniasis, bronchitis, allergic rhinitis, atopic dermatitis, cystic fibrosis, lung metabolism rejection, child rheumatoid arthritis, ankylosing spondylitis, pancreatitis, autoimmune diabetes mellitus, autoimmune eye disease, ulcerative colitis, sjorgen's syndrome, optic neuritis, diabetes mellitus, optic neuromyelitis, myasthenia gravis, uveitis, Guillain-Barre syndrome, psoriasis arthritis, Graves' disease and scleritis.

BRIEF DESCRIPTION OF THE DRAWINGS

FIG. 1 shows the in vivo activities of compounds of the present application and a solvent control in rat anti-arthritis CIA model.

DETAILED DESCRIPTION OF THE INVENTION

Unless otherwise defined, the meanings of all the scientific terms used herein are the same as those generally understood by a person skilled in the art to which the subject matter of the Claims pertains.

It is to be understood that the foregoing general description and the following detailed description are exemplary and are merely illustrative, and are not intended by any means to limit the subject matter of the present application.

All the documents or parts of the documents cited in the present application include, but are not limited to, patents, patent applications, articles, books, operating manuals and thesis, which are all incorporated herein by reference in their entirety.

Some chemical groups defined herein are preceded by shorthanded notations to represent the total numbers of carbon atoms or total numbers of ring atoms present in the groups. For example, $C_{1-8}$alkyl refers to an alkyl group as defined below having totally 1 to 8 carbon atoms; $C_{3-8}$ cycloalkyl refers to a cycloalkyl group as defined below having totally 3 to 8 carbon atoms; $C_{5-10}$aryl refers to an aryl group as defined below having totally 5 to 10 carbon atoms (or ring atoms). The total number of carbon atoms in the shorthanded notation does not include the carbon atom(s) that may be present in a substituent of the group. The term "member" used hereinbelow refers to the number of ring atoms in a group. For example, "5-membered aryl" means that the number of ring atoms in the aryl group is 5.

In addition to the foregoing, when used in the Description and Claims of the present application, the following terms have the meanings indicated below, unless otherwise indicated.

In the present application,

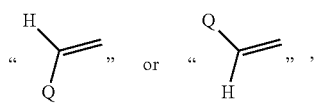

represents

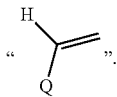

preferably

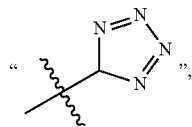 [SMILES: *C1N=NN=N1]

In the present application, C(=O) represents an acyl or carbonyl group, C(=O)OH represents a carboxyl group, $S(=O)_2$ represents a sulfonyl group, S(=O) represents a sulfinyl group, 5-tetrazole represents

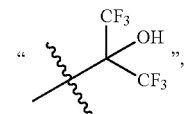

$HOC(CF_3)_2$ represents

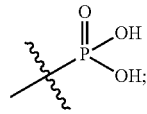

—OH represents a hydroxyl group, —$NH_2$ represents an amino group, —CN represents a cyano group, and —$NO_2$ represents a nitro group.

In the present application, the term "alkylsulfonyl" refers to $R^aS(=O)_2$, in which $R^a$ represents an alkyl group as defined below.

In the present application, the term "amido" refers to —C(=O)$NH_2$, RC(=O)NH— or RC(=O)N($R^a$)—, in which $R^a$ and R are each an alkyl group as defined herein (e.g. $C_{1-6}$ alkyl). Examples of the amido group include, but are not limited to, formamido, formamidomethyl, N-acetamido, N-methyl-N'-acetamido, and the like.

In the present application, the term "sulfonamide" refers to $R^aS(=O)_2NH$— or $R^aS(=O)_2NR^b$—, in which $R^a$ and $R^b$ are each an alkyl group as defined herein (e.g. $C_{1-6}$ alkyl).

In the present application, the term "aminosulfonyl" refers to —$S(=O)_2NH_2$, —$S(=O)_2NHR^a$ or —$S(=O)_2NR^aR^b$, in which $R^a$ and $R^b$ are each an alkyl group as defined herein (e.g. $C_{1-6}$ alkyl).

In the present application, the term "phosphoric acid group" refers to

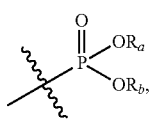

and the term "phosphate ester group" refers to in which $R^a$ and $R^b$ respectively represent alkyl groups as defined below.

In the present application, the term "halogen" refers to fluorine, chlorine, bromine or iodine, such as fluorine or chlorine.

In the present application, the term "alkyl", as a group or a part of another group (i.e., alkyl alone or attached to another group), is intended to mean a linear or branched group which consists only of carbon atom(s) and hydrogen atom(s), does not contain an unsaturated bond, and is linked to the remainder of the molecule by a single bond. The alkyl group may have, for example, from 1 to 18, from 1 to 8, from 1 to 6, from 1 to 4 carbon atoms. Examples of the alkyl group include, but are not limited to, methyl, ethyl, propyl, isopropyl, n-butyl, isobutyl, tert-butyl, n-pentyl, 2-pentyl, hexyl, heptyl, 2-methylhexyl, 3-methylhexyl, octyl, nonyl, decyl, and the like.

In the present application, the term "halogenated alkyl" refers to an alkyl group as defined above substituted by one or more halogen atoms. Examples of the halogenated alkyl group include, but are not limited to, trifluoromethyl, trichloromethyl, dichloromethyl, bromomethyl, iodomethyl, 1,2-dichloroethyl, and the like.

In the present application, the term "alkoxy" refers to a group of formula —$OR^a$, in which $R^a$ is an alkyl group as defined above. Examples of the alkoxy group include, but are not limited to, methoxy, ethoxy, isopropoxy, n-butoxy, isobutoxy, tert-butoxy, and the like.

In the present application, the term "halogenated alkoxy" refers to an alkoxy group substituted by one or more halogen atoms, in which alkoxy is as defined above.

In the present application, the term "alkylmercapto" refers to a group of formula —$SR^a$, in which $R^a$ is an alkyl group as defined above. Examples of the alkylmercapto group include, but are not limited to, methylmercapto, ethylmercapto, isopropylmercapto, and the like.

In the present application, the term "alkylamino" refers to a group of formula —$NHR^a$, in which $R^a$ is an alkyl group as defined above. Examples of the alkylamino group include, but are not limited to, methylamino, ethylamino, isopropylamino, and the like.

In the present application, the term "dialkylamino" refers to a group of formula —$NR^aR^b$, in which $R^a$ and $R^b$ are each independently an alkyl group as defined above. Examples of the dialkylamino group include, but are not limited to, dimethylamino, diethylamino, dipropylamino, methylethylamino, and the like.

In the present application, the term "alkylcarbonyl" refers to a group of formula —$COR^a$, in which $R^a$ is an alkyl group as defined above.

In the present application, the term "alkylaminocarbonyl" refers to —$CONHR^a$ or —$CONR^aR^b$, in which $R^a$ and $R^b$ are each an alkyl group as defined herein (e.g. $C_{1-6}$alkyl).

In the present application, the term "alkenyl", as a group or a part of another group, means a straight or branched hydrocarbon chain group which consists only of carbon atom(s) and hydrogen atom(s), contains at least one double bond, have for example from 2 to 14, from 2 to 10, from 2 to 8 carbon atoms, and is linked to the remainder of the molecule by a single bond, including, but not limited to, vinyl, propenyl, allyl, but-1-enyl, but-2-enyl, pent-1-enyl, pent-2-enyl, penta-1,4-dienyl, and the like.

In the present application, the term "alkynyl", as a group or a part of another group, means a straight or branched hydrocarbon chain group which consists only of carbon atom(s) and hydrogen atom(s), contains at least one triple bond and optionally one or more double bonds, have for example from 2 to 14, from 2 to 10, from 2 to 8 carbon atoms, and is linked to the remainder of the molecule by a single bond. Examples of the alkynyl group include, but are not limited to, ethynyl, prop-1-ynyl, pent-1-en-4-ynyl, and the like.

In the present application, the term "carbocyclyl", as a group or a part of another group, means a non-aromatic mono-cyclic or multi-cyclic hydrocarbon group consisting only of carbon atom(s) and hydrogen atom(s). It may include a fused ring system, a bridged ring system or a spiro ring system, have from 3 to 15 carbon atoms, preferably from 3 to 10 carbon atoms, from 3 to 8 carbon atoms, from 3 to 7 carbon atoms, and is saturated or unsaturated, and may be linked to the remainder of the molecule by a single bond via any suitable carbon atom. Unless otherwise indicated in this specification, the carbocyclyl group may be saturated (which may be referred to as cycloalkyl) or unsaturated (which may be referred to as cycloalkenyl). The carbon atom(s) in the cycloalkyl group may be optionally oxidized. Examples of the carbocyclyl group include, but are not limited to, cyclopropyl, cyclobutyl, cyclopentyl, cyclopentenyl, cyclohexyl, cyclohexenyl, cyclohexadienyl, cycloheptyl, cyclooctyl, 1H-indenyl, 2,3-indanyl, 1,2,3,4-tetrahydro-naphthyl, 5,6,7,8-tetrahydro-naphthyl, 8,9-dihydro-7H-benzocyclohepten-6-yl, 6,7,8,9-tetrahydro-5H-benzoheptenyl, 5,6,7,8,9,10-hexahydro-benzocyclooctenyl, fluorenyl, bicyclo[2.2.1]heptyl, 7,7-dimethyl-bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantyl, octahydro-4,7-methylene-1H-indenyl, octahydro-2,5-methylene-cyclopentadienyl, and the like.

In the present application, the term "heterocyclyl", as a group or a part of another group, means a 3- to 18-membered non-aromatic cyclic group consisting of from 2 to 12 carbon atoms and from 1 to 6 heteroatoms selected from the group consisting of nitrogen, oxygen and sulfur. The heterocyclic group may be saturated or unsaturated. Unless otherwise indicated in this specification, the heterocyclyl group may be a monocyclic, bicyclic, tricyclic or polycyclic ring system, which may include fused ring system or bridged ring system. For the purpose of the present application, the heterocyclyl group is preferably a 5- to 12-membered non-aromatic monocyclic or bicyclic group comprising from 1 to 3 heteroatoms selected from the group consisting of nitrogen, oxygen and sulfur, more preferably a 5- to 8-membered non-aromatic monocyclic group comprising from 1 to 3 heteroatoms selected from the group consisting of nitrogen, oxygen and sulfur, more preferably a 5- to 6-membered non-aromatic monocyclic group comprising from 1 to 2 heteroatoms selected from the group consisting of nitrogen, oxygen and sulfur. The nitrogen, carbon or sulfur atom in the heterocyclyl group may optionally be oxidized; the nitrogen atom may optionally be quaternized; and the heterocyclyl group may be partly or fully saturated. The heterocyclic group may be linked to the remainder of the molecule by a single bond via a carbon atom or a heteroatom. In a heterocyclic group comprising a fused ring, one or more of the rings may be aryl or heteroaryl, provided that the connection point with the remainder of the molecule is a non-aromatic ring atom. Examples of the heterocyclyl group include, but are not limited to, pyranyl, tetrahydropyranyl, thiapyranyl, tetrahydrofuranyl, morpholinyl, mercaptomorpholinyl, piperazinyl, piperidinyl, oxazinyl, dioxolanyl, tetrahydroisoquinolyl, decahydroisoquinolyl, imidazolinyl, imidazolidinyl, quinazolinyl, thiazolidinyl, isothiazolidinyl, isoxazolidinyl, dihydroindolyl, octahydroindolyl, octahydroisoindolyl, pyrrolidinyl, pyrazolidinyl, phthalimide, and the like, preferably tetrahydropyranyl, piperazinyl, morpholinyl.

In the present application, the term "aryl", as a group or a part of another group, means a system having from 6 to 18 (e.g. from 6 to 10, from 5 to 10) carbon atoms and at least one aromatic ring. For the present application, the aryl group may be a monocyclic, bicyclic, tricyclic or polycyclic ring system, which may comprise a fused or bridged ring system. The fused ring fused with the aryl group may be a carbocyclyl, heterocyclyl, aryl or heteroaryl group defined in the present application. The aryl group is linked to the remainder of the molecule by a single bond via an aromatic ring atom. Examples of the aryl group include, but are not limited to, phenyl, naphthyl, anthracenyl, phenanthrenyl, fluorenyl, 2-benzoxazolinone, 2H-1,4-benzoxazin-3(4H)-on-7-yl, and the like, preferably phenyl.

In the present application, the term "heteroaryl", as a group or a part of another group, means a 5- to 16-membered ring system having from 1 to 15 (e.g. from 1 to 10) carbon atoms and from 1 to 4 heteroatoms selected from the group consisting of nitrogen, oxygen and sulfur, as well as at least one aromatic ring. Unless otherwise indicated in this specification, the heteroaryl group may be a monocyclic, bicyclic, tricyclic or polycyclic ring system, which may comprise a fused or bridged ring system, provided that the connection point is an aromatic ring atom. The nitrogen, carbon or sulfur atom in the heteroaryl group may optionally be oxidized; and the nitrogen atom may optionally be quaternized. For the purpose of the present application, the heteroaryl group is preferably a 5- to 12-membered aromatic monocyclic or bicyclic group comprising from 1 to 3 heteroatoms selected from the group consisting of nitrogen, oxygen and sulfur, more preferably a 5- to 8-membered aromatic monocyclic or bicyclic group comprising from 1 to 3 heteroatoms selected from the group consisting of nitrogen, oxygen and sulfur, more preferably a 5- to 6-membered aromatic monocyclic or bicyclic group comprising from 1 to 2 heteroatoms selected from the group consisting of nitrogen, oxygen and sulfur. Examples of the heteroaryl group include, but are not limited to, thienyl, furanyl, pyrrolyl, [1,3,4]oxadiazolyl, [1,2,4]thiadiazolyl, [1,3,4]thiadiazolyl, imidazolyl, benzimidazolyl, pyrazolyl, benzopyrazolyl, triazolyl, tetrazolyl, pyridyl, pyrazinyl, triazinyl, pyrimidinyl, pyridazinyl, indolizinyl, indolyl, isoindolyl, indazolyl, isoindazolyl, purinyl, quinolyl, isoquinolyl, quinazolyl, naphthyridinyl, quinoxalinyl, pteridinyl, carbazolyl, carbolinyl, phenanthridinyl, phenanthrolinyl, acridinyl, phenazinyl, thiazolyl, isothiazolyl, benzothiazolyl, benzothienyl, oxazolyl, isoxazolyl, oxadiazolyl, oxatriazolyl, cinnolinyl, quinazolinyl, phenylmercapto, indolizinyl, phenanthrolinyl, phenoxazinyl, phenothiazinyl, 4,5,6,7-tetrahydrobenzo[b]thienyl, pyridopyridinyl, and the like.

"Stereoisomers" refer to compounds consisting of the same atoms, bonded by the same bonds, but having different three-dimensional structures. The present application will encompass various stereoisomers and mixtures thereof.

"Tautomers" refer to isomers formed by transferring a proton from one atom of a molecule to another atom of the same molecule. All the tautomeric forms of the compound of the present application will also be included in the scope of the present application.

As used herein, the term "pharmaceutically acceptable salt" refers to a salt which retains the biological efficacy of the free acid or free base of the compound of the present application, and does not have any adverse effect in biological or other aspects. A pharmaceutically acceptable salt refers to converting a basic group or an acidic group in a parent compound into a salt form. Pharmaceutically acceptable salts include, but are not limited to, inorganic or organic acid salts of basic groups such as amine (amino) groups. Pharmaceutically acceptable salts of the present application may be synthesized from a parent compound. Suitable salts are listed in Remingtong's Pharmaceutical Sciences, 17th ed., Mack Publishing Company, Easton, Pa., 1985, p. 1418 and Journal of Pharmaceutical Science, 66, 2(1977). Unless specifically indicated, the salt of the present application may be an acid salt formed from an organic acid/inorganic acid, and a base salt formed from an organic base/inorganic base. In addition, when the basic functional group of the general formula compound is pyridine or imidazole (but not limited thereto) and the acidic functional group is carboxylic acid (but not limited thereto), a zwitterion (inner salt) can be formed, and the inner salt is also included in the salt of the present application.

Depending on the number of charged functional groups and the valence of the cation or anion, the compound of the present application may contain a plurality of cations or anions.

In general, the crystallization action will produce the solvate of the compound of the present application. In the present application, "solvate" refers to an aggregate comprising one or more molecules of the compound of the present application and one or more solvent molecules. They either react in the solvent or precipitate or crystallize out from the solvent. The solvent may be water, in which case the solvate is a hydrate. Alternatively, the solvent may be an organic solvent. The solvate of the compound of the present application is also within the scope of the present application.

In the present application, the term "prodrug" represents a compound which can be converted to the biologically active compound of the present application under a physiological condition by hydrolysis or via an enzyme reaction. Accordingly, the term "prodrug" refers to a pharmaceutically acceptable metabolic precursor of the compound of the present application. The prodrug may be inactive when administered to an individual in need thereof, but is converted in vivo to the active compound of the present application. A prodrug is often converted rapidly in vivo to produce a parent compound of the present application, such as by hydrolysis in blood. Prodrug compounds generally provide advantages in solubility, histocompatibility or sustained release in mammal organisms. For reviews of prodrugs, see the following documents: Kevin Beaumont, et al., *Current Drug Metabolism*, 4(6), 461-485, 2003; Peter Ettmayer, et al., *Journal of Medicinal Chemistry*, 47(10), 2393-2404, 2004; Stella V. J., *Expert Opinion on Therapeutic Patents*, 14(3), 277-280, 2004; Jarkko Rautio, et al., *Nature Review Drug Discovery*, 7(3), 255-270, 2008. It would have been well known by a person skilled in the art that an ester, such as a pharmaceutically acceptable ester, of a compound comprising carboxyl group (e.g. the compounds of the present application), can be used as a prodrug of the compound of the present application, which can decompose to the parent acid in human body or animal body.

In the present application, a "pharmaceutical composition" refers to a formulation of a compound of the present application with a medium which is generally acceptable in the art for delivering a biologically active compound to a mammal (e.g. human). The medium includes pharmaceutically acceptable excipients.

In the present application, a "pharmaceutically acceptable excipient" includes, but is not limited to, any adjuvant, carrier, excipient, glidant, sweetener, diluent, preservative, dye/colorant, flavoring agent, surfactant, wetting agent, dispersing agent, suspending agent, stabilizer, isotonic agent, solvent or emulsifier, which is approved by a relevant government administration as acceptable for use in human or domestic animals.

In the present application, "preventively or therapeutically effective amount" refers to an amount of the compound of the present application, which is sufficient to effectively prevent or treat a disease in a mammal (e.g. human) when the compound of the present application is administered to a mammal (e.g., human). The amount of the compound of the present application which constitutes a "preventively or therapeutically effectively amount" depends on the specific compound used, the specific disorder to be treated, the cause of the disorder, the target of the drug, the severity of the disease, the administration means and the age, body weight, health conditions and the like of the mammal to be treated, but can be conventionally determined by a person skilled in the art according to his/her own knowledge and the disclosure of the present application.

As used herein, the term "prevention" includes reducing the possibility of the occurrence or deterioration of a disease or disorder.

As used herein, the term "treatment" includes the following meanings:

(1) preventing the occurrence of a disease or disorder in a mammal, especially when such mammal is susceptible to said disease or disorder, but has not been diagnosed to have said disease or disorder;

(2) inhibiting a disease or disorder, i.e., suppressing the development thereof;

(3) relieving a disease or disorder, i.e., causing the state of the disease or disorder to subside; or (4) alleviating the symptoms of a disease or disorder.

As used herein, the terms "disease" and "disorder" may be used interchangeably or may be different.

In the present application, the term "RORγ-mediated disease" refers to any disease or other harmful condition in which RORγ functions either by the generation of RORγ per se or the change in its activity level, or by causing the release of another monokine such as (but not limited to) IL-17 or IL-23.

In the present application, the term "RORγ modulator" refers to a molecule which interacts with and affects the function of the target RORγ, such interaction including, but not limited to: antagonism, agonism, inverse agonism and other similar interactions.

The compound of the present application or a pharmaceutically acceptable salt thereof may comprise one or more chiral carbon atoms. Each asymmetric carbon atom may be of R or S configuration, both configurations being within the scope of the present application. Accordingly, the compound may be present as an enantiomer, a diastereisomer, or a mixture thereof. The above-mentioned compound may be prepared by selecting a racemate, a diastereisomer or an enantiomer as a raw material or an intermediate. An optically active isomer may be prepared using a chiral synthon or a chiral reagent, or resolved by a conventional technology, for example by chiral chromatography or fractional crystallization.

Conventional techniques for preparing/separating individual isomers include chiral synthesis from a suitable optically pure precursor, or resolution of racemate (or racemate of a salt or a derivative) by using, for example chiral HPLC; see, for example, Gerald Gübitz and Martin G. Schmid (Eds.), Chiral Separations, Methods and Protocols, *Methods in Molecular Biology*, Vol. 243, 2004; A. M. Stalcup, Chiral Separations, *Annu. Rev. Anal. Chem.* 3:341-63, 2010; Fumiss et al. (eds.), VOGEL'S ENCYCLOPEDIA OF PRACTICAL ORGANIC CHEMISTRY 5. sup. TH Ed., Longman Scientific and Technical Ltd., Essex, 1991, 809-816; Heller, *Acc. Chem. Res.* 1990, 23, 128.

Another aspect of the present application relates to a pharmaceutical composition, which comprises one or more compounds of formula I of the present application, or a stereoisomer, a tautomer, a solvate or a pharmaceutically acceptable salt thereof, as well as a pharmaceutically acceptable excipient.

The pharmaceutical composition of the present application may be formulated as a solid, semi-solid, liquid or gaseous preparation, such as tablet, capsule, powder, granule, paste, solution, suppository, injection, inhalant, gel, microsphere and aerosol.

The pharmaceutical composition of the present application may be prepared by a method well known in the pharmacy field. For example, a pharmaceutical composition intended for injection administration may be prepared by combining a compound of the present application, or a pharmaceutically acceptable salt or a prodrug thereof, with sterilized distilled water to form a solution. A surfactant may be added to promote the formation of a uniform solution or suspension. The practical methods for preparing pharmaceutical compositions are known to a person skilled in the art. See, for example, *The Science and Practice of Pharmacy*, 20th Edition (Philadelphia College of Pharmacy and Science, 2000).

The administration routes of the pharmaceutical composition of the present application include, but are not limited to, oral, topical, transdermal, muscular, intravenous, inhalatory, parenteral, sublingual, rectal, vaginal and intranasal administrations. For example, dosage forms suitable for oral administration include capsule, tablet, granule, syrup, and the like. The compound of formula I of the present application included in these dosage forms may be solid powders or granules; a solution or suspension in an aqueous or non-aqueous liquid; water-in-oil or oil-in-water emulsion, and the like. The above-mentioned dosage forms may be prepared from an active compound and one or more carriers or adjuvants via a common pharmaceutical method. The above-mentioned carrier should be compatible with the active compound or other adjuvants. For solid preparations, commonly used non-toxic carriers include, but are not limited to, mannitol, lactose, starch, magnesium stearate, cellulose, glucose, sucrose and the like. The carriers for liquid preparations include, but are not limited to, water, normal saline, aqueous solution of glucose, ethylene glycol, polyethylene glycol, and the like. The active compound may be formulated into a solution or a suspension with the above carrier. The specific administration means and dosage forms depend on the physical and chemical properties of the compound per se and the severity of the disease to be treated. A person skilled in the art can determine the specific administration means according to the above factors in combination with his/her own knowledge. See, for example, LI Jun, "Clinical pharmacology", People's Medical Publishing House, 2008.06; DING Yufeng, Discussion on Clinical Dosage Form Factors and Drug Rational Use in Hospital, *Herald of Medicine*, 26(5), 2007; Howard C. Ansel, Loyd V. Allen, Jr., Nicholas G. Popovich, Eds., Translated by JIANG Zhiqiang, Pharmaceutical Dosage Forms and Drug Delivery Systems, China Medical Science Press, 2003.05.

The compound of the present application or the pharmaceutical composition of the present application may also be used in combination with one or more anti-inflammatory drugs. The anti-inflammatory drugs include, but are not limited to: NSAID, non-specific and specific cyclooxygenase-2 (COX-2) inhibitors, gold compounds, corticosteroids, tumor necrosis factor receptor antagonists, salicylate esters or salts, immunosuppressants and methotrexate.

The pharmaceutical composition of the present application is prepared, quantified and administered in a manner conforming to medical practice specifications. The "preventively or therapeutically effective amount" of the compound of the present application depends on factors such as the particular disorder to be treated, the individual to be treated, the cause of the disorder, the target of the drug, the administration means, and the like. In general, the dosage for parenteral administration may be 1-200 mg/kg, and the dosage for oral administration may be 1-1000 mg/kg.

The ranges of the effective dosages provided herein are not intended to limit the scope of the present application, but represent preferred dosage ranges. However, the most preferred dosage may be adjusted for individual subjects, which can be understood and determined by a person skilled in the art (see, for example, Berkow etc., Eds., The Merck Manual, 16th edition, Merck Co., Rahway, N. J., 1992).

SPECIFIC EMBODIMENTS

Preparation of the Compounds of the Present Application

Exemplary compounds of the present application can be prepared according to the following schemes. However, the following reaction schemes only exemplarily illustrate the preparation method of the compounds of the present application.

Those skilled in the art will appreciate that, in the following description, the combination of substituents are allowable only when such a combination leads to a stable compound.

Those skilled in the art will also appreciate that, in the methods described below, the functional group in the intermediate compound may need to be protected by an appropriate protective group. Such functional groups include hydroxyl, amino, mercapto and carboxyl. Suitable protective groups for the hydroxyl group include trialkylsilyl or diarylalkylsilyl (e.g. tert-butyldimethylsilyl, tert-butyldiphenylsilyl or trimethylsilyl), tetrahydropyranyl, benzyl, and the like. Suitable protective groups for the amino, amidinyl and guanidyl groups include t-butoxycarbonyl, benzyloxycarbonyl, and the like. Suitable protective groups for the mercapto group include —C(O)—R" (wherein R" is alkyl, aryl or arylalkyl), p-methoxybenzyl, triphenylmethyl, and the like. Suitable protective groups for the carboxyl group include alkyl, aryl or arylalkyl esters. The protective groups may be introduced and removed by standard techniques known to a person skilled in the art and as described herein. Use of protective groups is described in detail in Greene, T. W. and P. G. M. Wuts, Protective Groups in Organic Synthesis, (1999), $4^{th}$ Ed., Wiley. The protective groups can also be a polymer resin.

Scheme 1

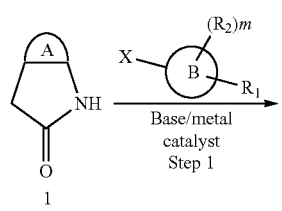

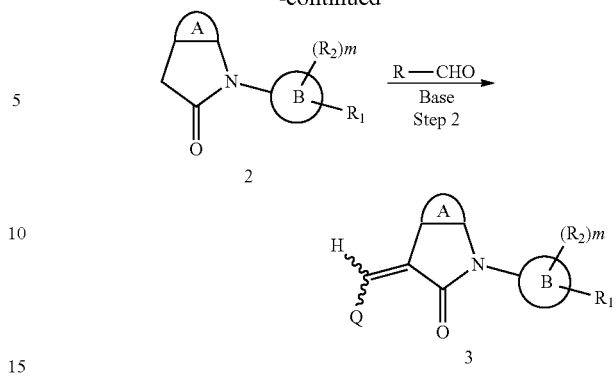

wherein R is a substituted 6-membered aryl ring or heteroaryl ring; m is 0, 1, 2, 3 or 4, preferably 0 or 1; X is I, Br, Cl, preferably I or Br; and the other variables are as previously described.

The synthesis of the compound of formula I of the present application is as follows (see Scheme 1). Substituted or un-substituted aryl- or heteroaryl-fused pyrrolid-2-one is used as a starting material, which is first reacted with a halogenated aromatic hydrocarbon or halogenated hydrocarbon (in which halogen is preferably iodine or bromine) shown in the scheme in the presence of a base (potassium carbonate or cesium carbonate, triethylamine, diisopropylethylamine, sodium hydride, or the like) as well as a metal catalyst (copper or palladium catalyst, preferably cuprous iodide) to give N-substituted aryl- or heteroaryl-fused pyrrolid-2-one intermediate, which is then subjected to a condensation reaction with a substituted aryl or heteroaryl aldehyde under a basic (piperidine, triethylamine, sodium alcoholate and the like, preferably piperidine) condition to give the target compound. The common synthetic route only represents a general method in most of the examples. For a compound with a special substituent, a modification which is known by a person with ordinary skill in the art can be made in a certain step. For example, in the synthesis in Example 1, there should be a last step in which the ester is hydrolyzed to give the carboxyl group (Step 3).

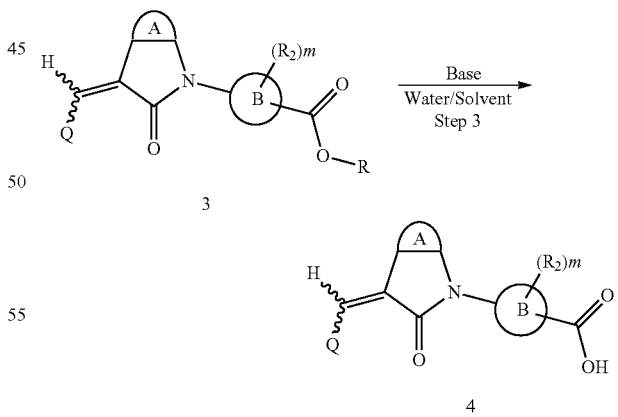

Here, the base refers to sodium hydroxide, lithium hydroxide, potassium hydroxide or the like, the solvent refers to methanol, ethanol, tetrahydrofuran, or the like, R is $C_{1-4}$ hydrocarbon, and the other groups are defined as above.

When a substituent is present in the starting material 1 in the above Scheme 1, alkyl, aryl, heteroaryl or the like may be introduced through Suzuki reaction (Route A):

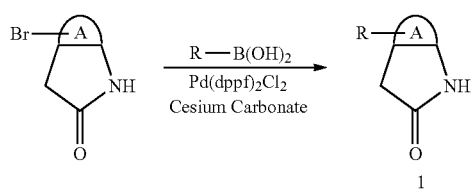

Here, R includes $C_{1-6}$ alkyl or cycloalkyl, aryl, heteroaryl.

When the aldehyde R—CHO used in the above Scheme 1 is a substituted benzaldehyde, the substituent such as alkyl, aryl or heteroaryl may be introduced through Suzuki reaction (Route B):

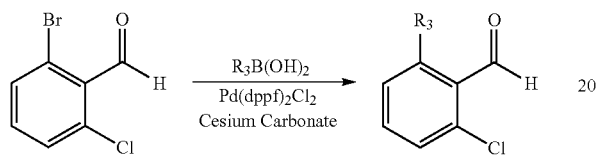

Here, $R_3$ includes $C_{1-6}$ alkyl or cycloalkyl, aryl, heteroaryl, preferably cyclopropyl.

When the starting material 1 used in the above Scheme 1 has a substituent $CF_3$ (2m), it may be synthesized according to the following route (Route C) by referring to the methods previously disclosed (Tetrahedron Letters, 43(50), 9175-9178, 2002; Synthesis, (1), 51-53, 1993):

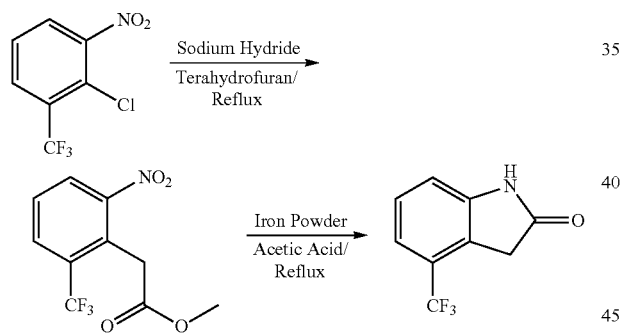

TABLE 1

| Raw materials | Chemical Structures | Sources |
|---|---|---|
| 1a | (cyclopropyl-substituted 2-chlorobenzaldehyde) | Route B |
| 1b | (2,6-dichlorobenzaldehyde) | Purchased |
| 1c | (2-chloro-6-trifluoromethylbenzaldehyde) | Purchased |
| 1d | (2-chloro-6-fluorobenzaldehyde) | Purchased |
| 1e | (2-bromo-6-chlorobenzaldehyde) | Purchased |
| 1f | (2-chloro-6-methoxybenzaldehyde) | Purchased |
| 1g | (2,6-difluorobenzaldehyde) | Purchased |
| 1h | (2-chloro-6-methylbenzaldehyde) | Purchased |
| 1i | (2-chloro-6-propylbenzaldehyde) | Route B |
| 1j | (2-chloro-6-cyclobutylbenzaldehyde) | Route B |
| 1k | (2-chloro-6-isopropylbenzaldehyde) | Route B |

TABLE 1-continued

| Raw materials | Chemical Structures | Sources |
|---|---|---|
| 1l | 2-ethyl-6-chlorobenzaldehyde | Purchased |
| 2a | 4-methylindolin-2-one | Purchased |
| 2b | 4-fluoroindolin-2-one | Purchased |
| 2c | 4-chloroindolin-2-one | Purchased |
| 2d | 4-methoxyindolin-2-one | Purchased |
| 2e | 4-cyclopropylindolin-2-one | Route A |
| 2f | 4-phenylindolin-2-one | Route A |
| 2g | 4-(trifluoromethyl)indolin-2-one | Route C |
| 2h | indolin-2-one | Purchased |
| 3a | methyl 2-hydroxy-4-iodobenzoate | Purchased |
| 3b | methyl 4-iodobenzoate | Purchased |
| 3c | methyl 2-chloro-4-iodobenzoate | Purchased |
| 3d | methyl 2-fluoro-4-iodobenzoate | Purchased |
| 3e | methyl 2-amino-4-iodobenzoate | Purchased |

The following examples illustrate the preparations and the biological activity evaluations of the compounds within the scope of the present application. The following examples and preparations are provided to enable a person skilled in the art to more clearly understand and practice the present application. They should not be construed as limiting the scope of the present application, but are merely illustrative and representative.

The starting materials used in the experiments of the present invention are either purchased from reagent suppliers or prepared from known raw materials through a well-known method in the art. Unless otherwise indicated, the examples herein employ the following conditions:

The temperature is in degree Celsius (° C.); and the room temperature is defined as 18-25° C.;

The organic solvents are dried on anhydrous magnesium sulfate or anhydrous sodium sulfate; and the solvents are evaporated to dryness under reduced pressure and elevated temperature (e.g. 15 mmHg, 30° C.) using a rotary evaporator;

200-300 mesh silica gel is used as the stationary phase in the column chromatographic separation, and TLC represents thin layer chromatography;

Generally, the progress of the reactions is monitored by TLC or LC-MS; and

The final products are characterized by nuclear magnetic resonance (Bruker AVANCE 300, 300 MHz) and LC-MS (Bruker esquine 6000, Agilent 1200 series).

Example 1: (trans)-4-(3-(2-chloro-6-cyclopropyl-benzylidene)-4-methylindolin-2-on-1-yl)-2-hydroxy benzoic acid

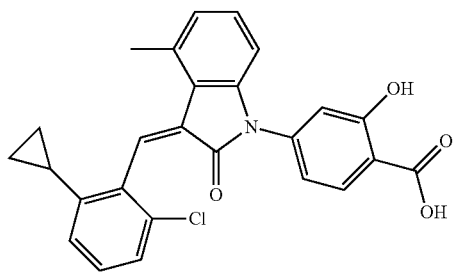 [SMILES: Cc1cccc2c1/C(=C/c1c(Cl)cccc1C1CC1)C(=O)N2c1ccc(C(=O)O)c(O)c1]

The compound of Example 1 is synthesized from (1-1) as a starting material, and the detailed route is as follows:

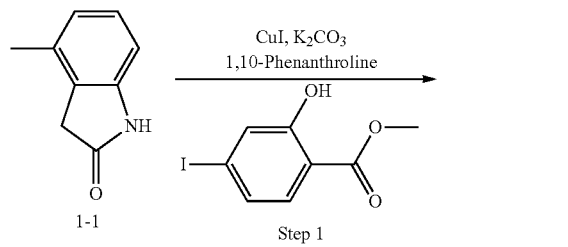

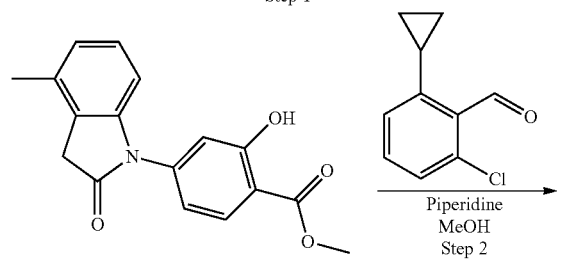

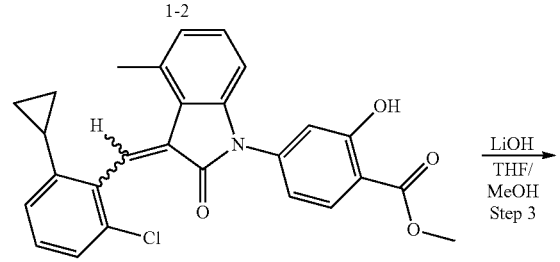

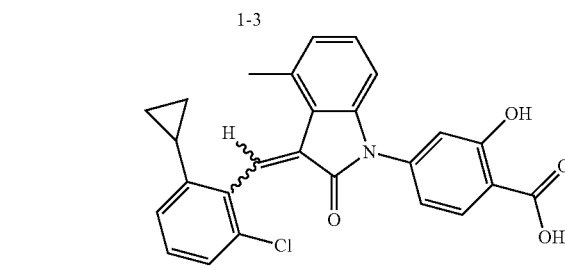

Step 1: synthesis of methyl 4-(4-methylindolin-2-on)ylsalicylate (1-2)

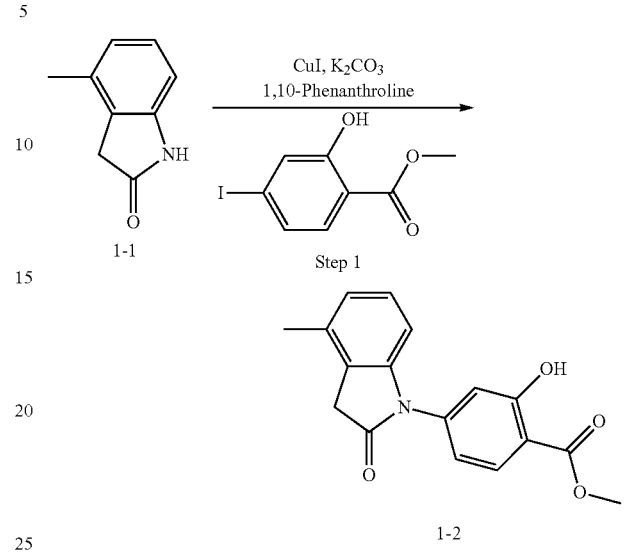

4-Methylindol-2-one (147 mg, 1 mmol) and methyl 4-iodosalicylate (306 mg, 1.1 mmol) were dissolved in 2 mL dioxane, followed by adding cuprous iodide (38 mg, 0.2 mmol), 1,10-phenanthroline (54 mg, 0.3 mmol) and potassium carbonate (415 mg, 3 mmol). The mixture was heated by microwave at 125° C. to react for 120 min. The mixture was cooled to room temperature, diluted with 20 mL ethyl acetate, filtered, and evaporated under reduced pressure to remove the solvent. The residue was separated by column chromatography (silica gel 200-300 mesh, eluent: n-hexane/ethyl acetate=4/1) to give 70 mg methyl 4-(4-methylindolin-2-on)-ylsalicylate as a yellow solid with a yield of 23.5%.

(2) Step 2: synthesis of methyl 4-(3-(2-chloro-6-cyclopropyl-benzylidene)-4-methyl indolin-2-on-1-yl)-2-hydroxybenzoate (1-3)

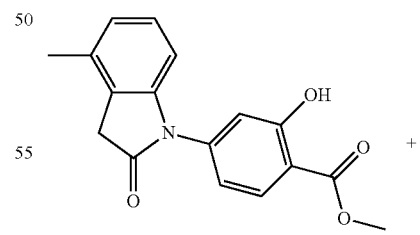

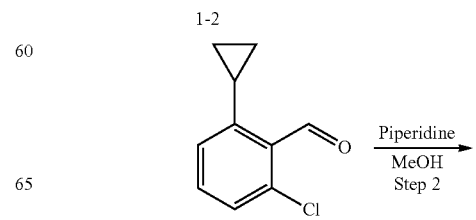

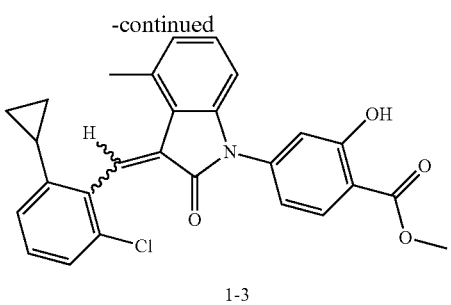

1-3

Methyl 4-(4-Methyl-indolin-2-on)-ylsalicylate (2, 70 mg, 0.24 mmol), 2-chloro-6-cyclopropyl benzaldehyde (85 mg, 0.48 mmol) and piperidine (22 mg, 0.24 mmol) were dissolved in methanol (5 mL), and heated to reflux for two hours under nitrogen protection. The mixture was cooled down to room temperature, evaporated under reduced pressure to remove the solvent, and subjected to column chromatography (silica gel 200-300 mesh, eluent: n-hexane/ethyl acetate=4/1) to give 88 mg methyl 4-(3-(2-chloro-6-cyclopropyl-benzylidene)-4-methylindolin-2-on-1-yl)-2-hydroxybenzoate with a yield of 80%.

(3) Step 3: synthesis of 4-(3-(2-chloro-6-cyclopropyl-benzylidene)-4-methylindolin-2-on-1-yl)-2-hydroxybenzoic acid (Example 1)

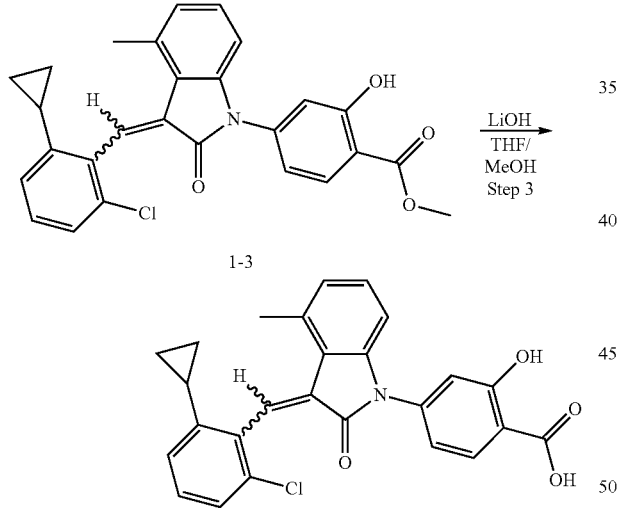

Methyl 4-(3-(2-chloro-6-cyclopropylbenzylidene)-4-methylindolin-2-on-1-yl)-2-hydroxy benzoate (1-3, 88 mg, 0.19 mmol) was dissolved in tetrahydrofuran (10 mL), to which was added an aqueous solution (1 mL) of lithium hydroxide (40 mg) at room temperature. The mixture was stirred overnight at room temperature. The mixture was evaporated under reduced pressure to remove the solvent. The residue was dissolved in water, and pH of the system was adjusted with 1 mol/L hydrochloric acid to 5. The mixture was extracted with ethyl acetate, concentrated under reduced pressure, and purified with prep-HPLC to give 45 mg compound of Example 1 as light yellow powder with a yield of 53%.

Relevant characterization data are as follows: ESI-MS: [M+H]$^+$=446.3

$^1$H-NMR (300 MHz, DMSO-d$_6$) δ: ppm 7.91 (d, J=9.0 Hz, 1H), 7.87 (s, 1H), 7.22-7.31 (m, 3H), 6.95-7.03 (m, 4H), 6.81 (d, J=7.8 Hz, 1H), 2.64 (s, 3H), 1.89-1.99 (m, 1H), 0.84-0.87 (m, 2H), 0.64-0.70 (m, 2H).

Example 2

The preparation of the compound of this example was similar to the method described in Example 1, except that the raw material 3a in Step 1 was replaced by the raw material 3b in Table 1, and the following compounds were obtained:

(trans)-4-(3-(2-chloro-6-cyclopropyl-benzylidene)-4-methylindolin-2-on-1-yl)-benzoic acid (2A)

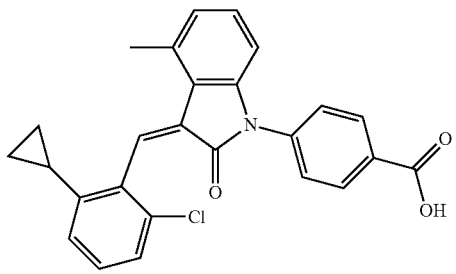 [SMILES: Cc1cccc2c1/C(=C/c1c(Cl)cccc1C1CC1)C(=O)N2c1ccc(C(=O)O)cc1]

Relevant characterization data are as follows: ESI-MS: [M+H]$^+$=430.3

$^1$H-NMR (300 MHz, DMSO-d$_6$) δ: ppm 8.03 (d, 2H, J=8.7 Hz), 7.84 (s, 1H), 7.50 (d, 2H, J=8.7 Hz), 7.22 (m, 3H), 6.96 (q, 2H, J=7.8 Hz), 6.73 (d, 1H, J=7.8 Hz), 2.60 (s, 3H), 1.87 (m, 1H), 0.81 (m, 2H), 0.62 (m, 2H); and (trans)-4-(3-(2-chloro-6-cyclopropyl-benzylidene)-4-methylindolin-2-on-1-yl)-benzoic acid (2B)

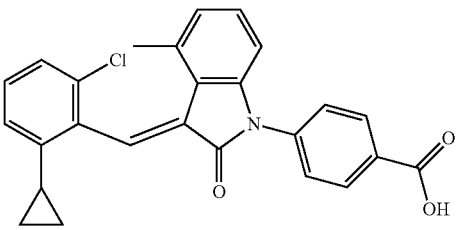 [SMILES: Cc1cccc2c1/C(=C\c1c(Cl)cccc1C1CC1)C(=O)N2c1ccc(C(=O)O)cc1]

Relevant characterization data are as follows: ESI-MS: [M+H]$^+$=430.2

$^1$H-NMR (300 MHz, DMSO-d$_6$) δ: ppm 8.03 (d, 2H, J=8.7 Hz), 7.84 (s, 1H), 7.50 (d, 2H, J=8.7 Hz), 7.22 (m, 3H), 6.96 (q, 2H, J=7.8 Hz), 6.73 (d, 1H, J=7.8 Hz), 2.60 (s, 3H), 1.87 (m, 1H), 0.81 (m, 2H), 0.62 (m, 2H).

Example 3

The preparation of the compound of this example was similar to the method described in Example 1, except that the raw material 1a in Step 2 was replaced by the raw material 1f in Table 1, and (trans)-4-(3-(2-chloro-6-methoxy-benzylidene)-4-methylindolin-2-on-1-yl)-2-hydroxybenzoic acid was obtained

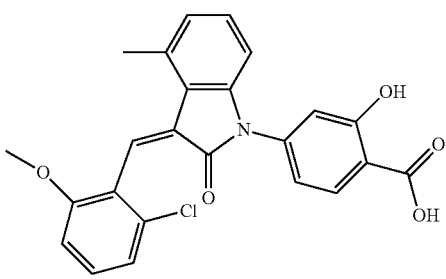 [SMILES: COc1cccc(Cl)c1/C=C1\C(=O)N(c2ccc(C(=O)O)c(O)c2)c2cccc(C)c21]

Relevant characterization data are as follows: ESI-MS: [M+H]⁺=436.3

¹H-NMR (300 MHz, DMSO-d₆) δ: ppm 7.92 (dd, J=7.5 Hz, J=1.2 Hz, 1H), 7.59 (s, 1H), 7.35 (t, J=8.1 Hz, 1H), 7.24 (t, J=7.8 Hz, 1H), 6.96-7.11 (m, 5H), 6.80 (d, J=8.1 Hz, 1H), 3.77 (s, 3H), 2.59 (s, 3H).

Example 4

The preparation of the compound of this example was similar to the method described in Example 1, except that the raw material 1a in Step 2 was replaced by the raw material 1b in Table 1, and (trans)-4-(3-(2,6-dichloro-benzylidene)-4-methylindolin-2-on-1-yl)-2-hydroxybenzoic acid was obtained.

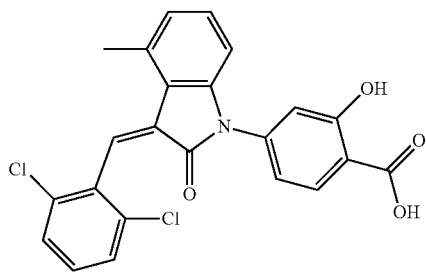 [SMILES: Cc1cccc2c1/C(=C/c1c(Cl)cccc1Cl)C(=O)N2c1ccc(C(=O)O)c(O)c1]

Relevant characterization data are as follows: ESI-MS: [M+H]⁺=440.2

¹H-NMR (300 MHz, DMSO-d₆) δ: ppm 7.91 (d, 1H, J=8.1 Hz), 7.70 (s, 1H), 7.52 (d, 2H, J=7.8 Hz), 7.36-7.42 (m, 1H), 7.27 (t, 1H, J=7.8 Hz), 7.03 (d, 1H, J=7.8 Hz), 6.93-6.97 (m, 2H), 6.81 (d, 1H, J=8.1 Hz), 2.61 (s, 3H).

Example 5

The preparation of the compound of this example was similar to the method described in Example 1, except that the raw material 3a in Step 1 was replaced by the raw material 3b in Table 1, and the raw material 1a in Step 2 was replaced by the raw material 1b in Table 1, and (trans)-4-(3-(2,6-dichlorobenzylidene)-4-methylindolin-2-on-1-yl)-benzoic acid was obtained.

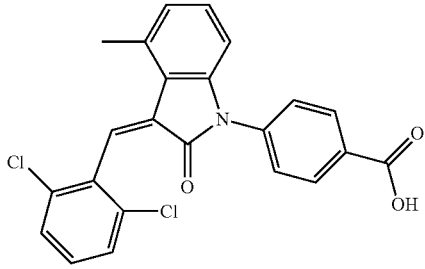 [SMILES: Cc1cccc2c1/C(=C/c1c(Cl)cccc1Cl)C(=O)N2c1ccc(C(=O)O)cc1]

Relevant characterization data are as follows: ESI-MS: [M+H]⁺=424.1

¹H-NMR (300 MHz, CDCl₃) δ: ppm 8.19 (d, J=8.4 Hz, 2H), 7.57 (s, 1H), 7.55 (d, J=8.1 Hz, 2H), 7.36 (d, J=7.8 Hz, 2H), 7.21 (t, 2H), 6.98 (d, J=7.8 Hz, 1H), 6.83 (d, J=7.8 Hz, 1H), 2.69 (s, 3H).

Example 6

The preparation of the compound of this example was similar to the method described in Example 1, except that the raw material 1a in Step 2 was replaced by the raw material 1c in Table 1, and (trans)-4-(3-(2-chloro-6-(trifluoromethyl)-benzylidene)-4-methyl indolin-2-on-1-yl)-2-hydroxybenzoic acid was obtained.

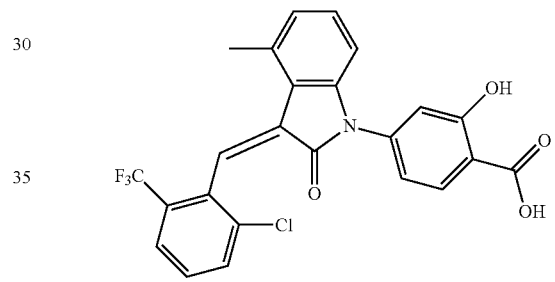

Relevant characterization data are as follows: ESI-MS: [M+H]⁺=474.2

¹H-NMR (300 MHz, CD₃OD-d₄) δ: ppm 7.95 (d, 1H, J=8.1 Hz), 7.69 (m, 3H), 7.46 (m, 1H), 7.21 (m, 1H), 7.00 (m, 1H), 6.86 (s, 1H), 6.77 (d, 1H, J=7.8 Hz), 2.59 (s, 3H).

Example 7

The preparation of the compound of this example was similar to the method described in Example 1, except that the raw material 1a in Step 2 was replaced by the raw material 1e in Table 1, and (trans)-4-(3-(2-chloro-6-bromo-benzylidene)-4-methylindolin-2-on-1-yl)-2-hydroxybenzolic acid was obtained.

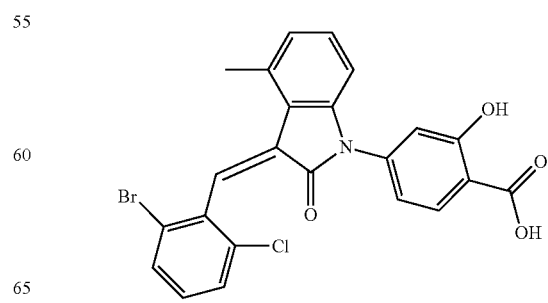

Relevant characterization data are as follows: ESI-MS: [M+H]⁺=486.1

¹H-NMR (300 MHz, CDCl₃) δ: ppm 7.98 (d, 1H, J=8.4 Hz), 7.58 (d, 2H, J=5.4 Hz), 7.45 (d, 1H, J=8.1 Hz), 7.14-7.25 (m, 3H), 7.00-7.08 (m, 2H), 6.93 (d, 1H, J=8.1 Hz), 2.72 (s, 3H).

Example 8

The preparation of the compound of this example was similar to the method described in Example 1, except that the raw material 2a in Step 1 was replaced by the raw material 2d in Table 1, and (trans)-4-(3-(2-chloro-6-bromo-benzylidene)-4-methoxyindolin-2-on-1-yl)-2-hydroxybenzolic acid was obtained.

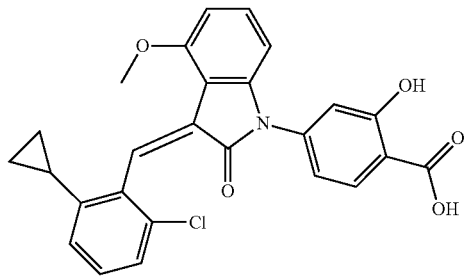 [SMILES: COc1cccc2c1/C(=C/c1c(Cl)cccc1C1CC1)C(=O)N2c1ccc(C(=O)O)c(O)c1]

Relevant characterization data are as follows: ESI-MS: [M+H]⁺=462.2

¹H-NMR (300 MHz, DMSO-d₆) δ: ppm 8.06 (s, 1H), 7.91 (d, J=9.3 Hz, 1H), 7.21-7.36 (m, 3H), 6.89-6.98 (m, 4H), 6.60 (d, J=7.8 Hz, 1H), 4.02 (s, 3H), 1.85-1.94 (m, 1H), 0.85-0.88 (m, 2H), 0.58-0.75 (m, 2H).

Example 9

The preparation of the compound of this example was similar to the method described in Example 1, except that the raw material 1a in Step 2 was replaced by the raw material 1g in Table 1, and (trans)-4-(3-(2-chloro-6-bromo-benzylidene)-4-methylindolin-2-on-1-yl)-2-hydroxybenzoic acid was obtained.

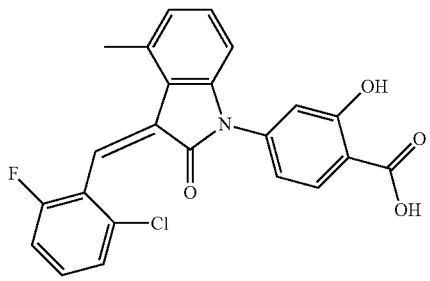 [SMILES: Cc1cccc2c1/C(=C/c1c(F)cccc1Cl)C(=O)N2c1ccc(C(=O)O)c(O)c1]

Relevant characterization data are as follows: ESI-MS: [M+H]⁺=424.2

¹H-NMR (300 MHz, DMSO-d₆) δ: ppm 7.55 (s, 1H), 7.15-7.33 (m, 4H), 7.03-7.06 (m, 1H), 6.94 (d, J=7.8 Hz, 1H), 6.80-6.84 (m, 2H), 6.72 (d, J=7.8 Hz, 1H), 2.60 (s, 3H).

Example 10

The preparation of the compound of this example was similar to the method described in Example 1, except that the raw material 1a in Step 2 was replaced by the raw material 1h in Table 1, and (trans)-4-(3-(2-chloro-6-methyl-benzylidene)-4-methylindolin-2-on-1-yl)-2-hydroxybenzoic acid was obtained.

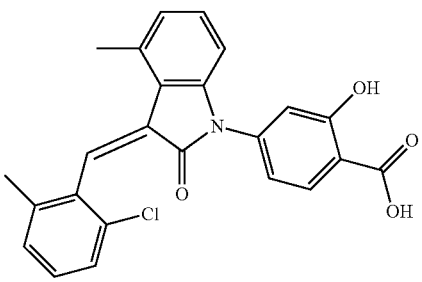 [SMILES: Cc1cccc(Cl)c1/C=C1\C(=O)N(c2ccc(C(=O)O)c(O)c2)c2cccc(C)c21]

Relevant characterization data are as follows: ESI-MS: [M+H]⁺=420.3

¹H-NMR (300 MHz, DMSO-d₆) δ: ppm 7.89 (d, 1H, J=8.1 Hz), 7.77 (s, 1H), 7.22-7.34 (m, 4H), 6.94-7.03 (m, 3H), 6.79 (d, 1H, J=7.8 Hz), 2.63 (s, 3H), 2.28 (s, 3H).

Example 11

The preparation of the compound of this example was similar to the method described in Example 1, except that the raw material 2a in Step 1 was replaced by the raw material 2d in Table 1, and the raw material 1a in Step 2 was replaced by the raw material 1b, and (trans)-4-(3-(2,6-dichloro-benzylidene)-4-methoxyindolin-2-on-1-yl)-2-hydroxybenzolic acid was obtained.

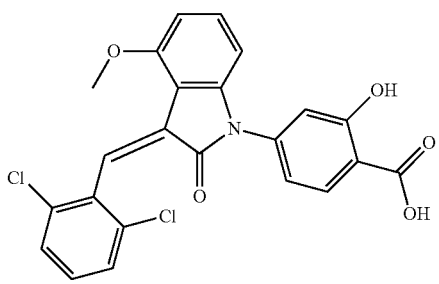 [SMILES: COc1cccc2c1/C(=C/c1c(Cl)cccc1Cl)C(=O)N2c1ccc(C(=O)O)c(O)c1]

Relevant characterization data are as follows: ESI-MS: [M+H]⁺=456.2

¹H-NMR (300 MHz, DMSO-d₆) δ: ppm 7.85-7.80 (m, 1H), 7.55-7.30 (m, 5H), 6.91-6.78 (m, 3H), 6.57-6.54 (m, 1H), 5.97-5.95 (m, 1H), 4.01 (s, 3H).

Example 12

The preparation of the compound of this example was similar to the method described in Example 1, except that the raw material 2a in Step 1 was replaced by the raw material 2e in Table 1, and (trans)-4-(3-(2-chloro-6-cyclopropyl-benzylidene)-4-cyclopropyl indolin-2-on-1-yl)-2-hydroxybenzolic acid was obtained.

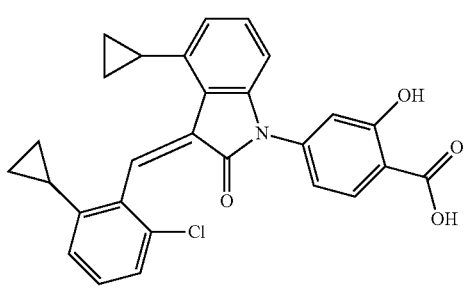 [SMILES: O=C(O)c1ccc(N2C(=O)/C(=C\c3c(Cl)cccc3C3CC3)c3c(C4CC4)cccc32)cc1O]

Relevant characterization data are as follows: ESI-MS: [M+H]⁺=472.2

¹H-NMR (300 MHz, CD₃OD-d₄) δ: ppm 8.35 (s, 1H), 7.98 (d, 1H, J=9.0 Hz), 7.24 (m, 3H), 6.91-7.07 (m, 4H), 6.81 (d, 1H, J=7.8 Hz), 2.22 (m, 1H), 1.98 (m, 1H), 1.13 (m, 2H), 0.88 (m, 4H), 0.72 (m, 1H), 0.63 (m, 1H).

Example 13

The preparation of the compound of this example was similar to the method described in Example 1, except that the raw materials 2a and 3a in Step 1 were replaced by the raw materials 2f and 3b in Table 1, respectively, and (trans)-4-(3-(2-chloro-6-cyclopropyl-benzylidene)-4-phenylindolin-2-on-1-yl)-2-hydroxy benzolic acid was obtained.

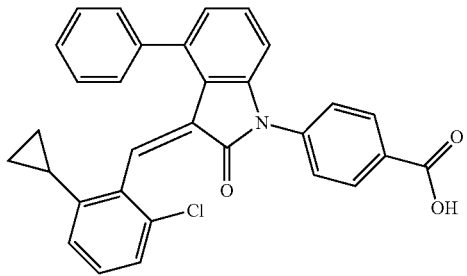 [SMILES: O=C(O)c1ccc(N2C(=O)/C(=C\c3c(Cl)cccc3C3CC3)c3c(-c4ccccc4)cccc32)cc1]

Relevant characterization data are as follows: ESI-MS: [M+H]⁺=492.3

¹H-NMR (300 MHz, DMSO-d₆) δ: ppm 8.18-8.08 (m, 2H), 7.78-7.14 (m, 10H), 7.02-6.87 (m, 4H), 1.54-1.50 (m, 1H), 1.29-1.17 (m, 2H), 0.85-0.75 (m, 2H).

Example 14

The preparation of the compound of this example was similar to the method described in Example 1, except that the raw material 2a in Step 1 was replaced by the raw material 2c in Table 1, and 4-(3-(2-chloro-6-cyclopropyl-benzylidene)-4-chloro-indolin-2-on-1-yl)-2-hydroxybenzolic acid was obtained.

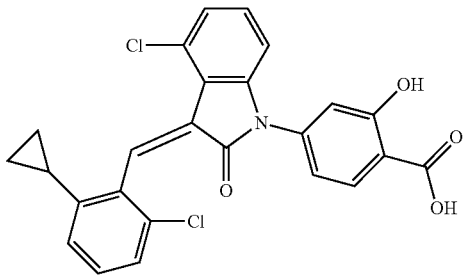 [SMILES: O=C(O)c1ccc(N2C(=O)/C(=C\c3c(Cl)cccc3C3CC3)c3c(Cl)cccc32)cc1O]

Relevant characterization data are as follows: ESI-MS: [M+H]⁺=466.2

¹H-NMR (300 MHz, DMSO-d₆) δ: ppm 8.46-7.94 (m, 1H), 7.79-7.76 (m, 1H), 7.35-7.19 (m, 4H), 7.10-6.79 (m, 2H), 6.76-6.60 (m, 2H), 1.71-1.69 (m, 1H), 1.29-1.23 (m, 2H), 0.88-0.83 (m, 2H).

Example 15

The preparation of the compound of this example was similar to the method described in Example 1, except that the raw materials 2a and 3a in Step 1 were replaced by the raw materials 2b and 3b in Table 1, respectively, and the raw material 1a in Step 2 was replaced by the raw material 1b, and the following compounds were obtained:

(trans)-4-(3-(2,6-dichloro-benzylidene)-4-fluoro-indolin-2-on-1-yl)-benzoic acid (15A)

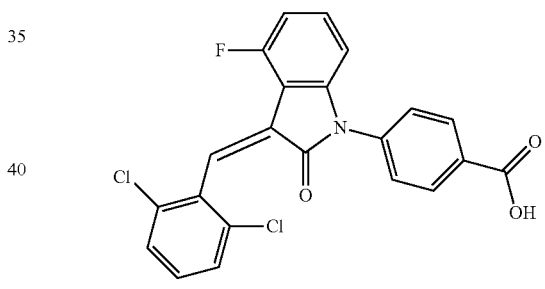

Relevant characterization data are as follows: ESI-MS: [M+H]⁺=427.8

¹H-NMR (CDCl₃) δ: ppm 8.21 (d, J=8.4 Hz, 2H), 7.78 (d, J=1.5 Hz, 1H), 7.57 (d, J=8.7 Hz, 2H), 7.39-7.35 (m, 2H), 7.31-7.20 (m, 2H), 6.93-6.87 (m, 1H), 6.78 (d, J=7.8 Hz, 1H); and (cis)-4-(3-(2,6-dichloro-benzylidene)-4-fluoro-indolin-2-on-1-yl)-benzoic acid (15B)

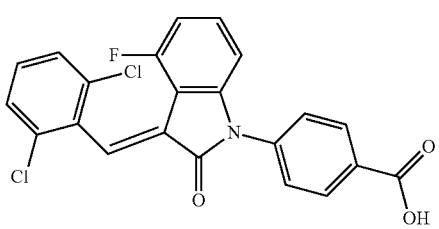 [SMILES: O=C(O)c1ccc(N2C(=O)/C(=C/c3c(Cl)cccc3Cl)c3c(F)cccc32)cc1]

Relevant characterization data are as follows: ESI-MS: [M+H]+=427.8

¹H-NMR (CDCl₃) δ: ppm 8.30 (d, J=8.4 Hz, 2H), 7.90 (s, 1H), 7.65 (d, J=8.7 Hz, 2H), 7.42-7.38 (m, 2H), 7.32-7.29 (m, 1H), 7.25-7.19 (m, 1H), 7.75-6.65 (m, 2H).

Example 16

The preparation of the compound of this example was similar to the method described in Example 1, except that the raw materials 2a and 3a in Step 1 were replaced by the raw materials 2b and 3b in Table 1, respectively, and the following compounds were obtained:

(trans)-4-(3-(2-chloro-6-cyclopropyl-benzylidene)-4-fluoro-indolin-2-on-1-yl)-benzoic acid (16A)

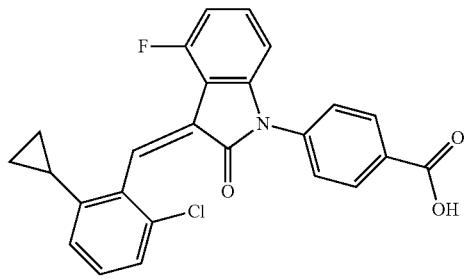 [SMILES: O=C(O)c1ccc(N2C(=O)/C(=C\c3c(Cl)cccc3C3CC3)c3c(F)cccc32)cc1]

Relevant characterization data are as follows: ESI-MS: [M+H]+=433.9

¹H-NMR (300 MHz, CDCl₃) δ: ppm 8.20 (d, 2H, J=8.7 Hz), 8.04 (s, 1H), 7.56 (d, 2H, J=8.4 Hz), 7.27 (m, 2H), 7.19 (m, 1H), 6.90 (m, 2H), 6.79 (d, 1H, J=7.8 Hz), 1.92 (m, 1H), 0.88 (m, 3H), 0.61 (m, 1H); and (cis)-4-(3-(2-chloro-6-cyclopropyl-benzylidene)-4-fluoro-indolin-2-on-1-yl)-benzoic acid (16B)

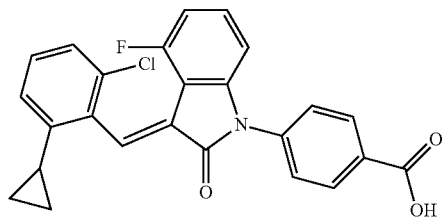 [SMILES: O=C(O)c1ccc(N2C(=O)/C(=C/c3c(Cl)cccc3C3CC3)c3c(F)cccc32)cc1]

Relevant characterization data are as follows: ESI-MS: [M+H]+=433.9

¹H-NMR (300 MHz, CDCl₃) δ: ppm 8.20 (d, 2H, J=8.7 Hz), 8.04 (s, 1H), 7.56 (d, 2H, J=8.4 Hz), 7.27 (m, 2H), 7.20 (d, 1H, J=8.1 Hz), 6.90 (m, 2H), 6.89 (d, 1H, J=7.8 Hz), 1.92 (m, 1H), 0.83 (m, 3H), 0.59 (m, 1H).

Example 17

The preparation of the compound of this example was similar to the method described in Example 1, except that the raw materials 2a and 3a in Step 1 were replaced by the raw materials 2b and 3b in Table 1, respectively, and the raw material 1a in Step 2 was replaced by the raw material 1g, and the following compounds were obtained:

(trans)-4-(3-(2-chloro-6-fluoro-benzylidene)-4-fluoro-indolin-2-on-1-yl)-benzoic acid (17A)

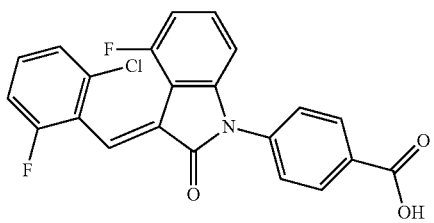 [SMILES: O=C(O)c1ccc(N2C(=O)/C(=C/c3c(F)cccc3Cl)c3c(F)cccc32)cc1]

Relevant characterization data are as follows: ESI-MS: [M+H]+=411.9

¹H-NMR (300 MHz, CDCl₃) δ: ppm 8.30 (d, 2H, J=8.4 Hz), 7.88 (s, 1H), 7.62 (d, 2H, J=8.7 Hz), 7.21-7.37 (m, 3H), 7.09 (t, 1H, J=8.7 Hz), 6.73 (d, 2H, J=8.1 Hz); and (cis)-4-(3-(2-chloro-6-fluoro-benzylidene)-4-fluoro-indolin-2-on-1-yl)-benzoic acid (17B)

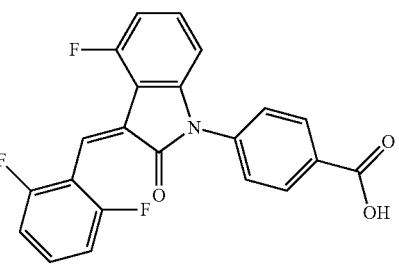

Relevant characterization data are as follows: ESI-MS: [M+H]+=411.9

¹H-NMR (300 MHz, CDCl₃) δ: ppm 8.22 (d, 2H, J=8.4 Hz), 7.76 (s, 1H), 7.56 (d, 2H, J=8.4 Hz), 7.22-7.31 (m, 3H), 7.05 (t, 1H, J=8.7 Hz), 6.88 (t, 1H, J=9.0 Hz), 6.75 (d, 1H, J=7.8 Hz).

Example 18

The preparation of the compound of this example was similar to the method described in Example 1, except that the raw materials 2a and 3a in Step 1 were replaced by the raw materials 2b and 3b in Table 1, and the raw material 1a in Step 2 was replaced by the raw material 1d, and the following compounds were obtained:

(trans)-4-(3-(2,6-difluoro-benzylidene)-4-fluoro-indolin-2-on-1-yl)-benzoic acid (18A)

Relevant characterization data are as follows: ESI-MS: [M+H]⁺=396.1

¹H-NMR (300 MHz, DMSO-d₆) δ: ppm 8.15-8.08 (m, 2H), 7.68-7.66 (m, 2H), 7.60-7.39 (m, 3H), 7.27-6.87 (m, 3H), 6.78-6.73 (m, 1H); and (cis)-4-(3-(2,6-difluoro-benzylidene)-4-fluoro-indolin-2-on-1-yl)-benzoic acid (18B)

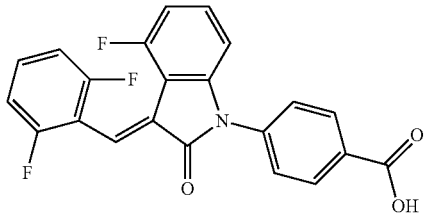 [SMILES: O=C(O)c1ccc(N2C(=O)/C(=C/c3c(F)cccc3F)c3c(F)cccc32)cc1]

Relevant characterization data are as follows: ESI-MS: [M+H]⁺=396.1

¹H-NMR (300 MHz, DMSO-d₆) δ: ppm 8.15-8.08 (m, 2H), 7.69-7.57 (m, 4H), 7.41-6.88 (m, 4H), 6.78-6.73 (m, 1H).

Example 19

The preparation of the compound of this example was similar to the method described in Example 1, except that the raw materials 2a and 3a in Step 1 were replaced by the raw materials 2b and 3b in Table 1, respectively, and the raw material 1a in Step 2 was replaced by the raw material 1c, and the following compounds were obtained:

(trans)-4-(3-(2-chloro-6-trifluoromethyl-benzylidene)-4-fluoro-indolin-2-on-1-yl)-benzoic acid (19A)

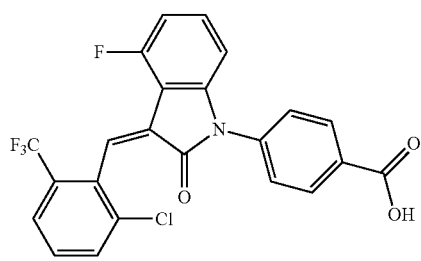 [SMILES: O=C(O)c1ccc(N2C(=O)/C(=C\c3c(Cl)cccc3C(F)(F)F)c3c(F)cccc32)cc1]

Relevant characterization data are as follows: ESI-MS: [M+H]⁺=462.1

¹H-NMR (300 MHz, DMSO-d₆) δ: ppm 13.11 (brs, 1H), 8.16-8.13 (d, 2H), 7.90-7.79 (m, 3H), 7.64-7.58 (t, 1H), 7.55-7.52 (d, 1H), 7.45-7.40 (m, 1H), 7.13-7.07 (t, 1H), 6.83-6.80 (d, 1H); and (cis)-4-(3-(2-chloro-6-trifluoromethyl-benzylidene)-4-fluoro-indolin-2-on-1-yl)-benzoic acid (19B)

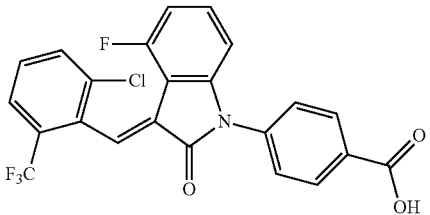 [SMILES: O=C(O)c1ccc(N2C(=O)/C(=C/c3c(Cl)cccc3C(F)(F)F)c3c(F)cccc32)cc1]

Relevant characterization data are as follows: ESI-MS: [M+H]⁺=462.1

¹H-NMR (300 MHz, DMSO-d₆) δ: ppm 13.14 (brs, 1H), 8.15-8.13 (d, 2H), 7.93-7.84 (m, 3H), 7.72-7.65 (m, 3H), 7.40-7.33 (m, 1H), 6.83-6.73 (m, 2H).

Example 20

The preparation of the compound of this example was similar to the method described in Example 1, except that the raw materials 2a and 3a in Step 1 were replaced by the raw materials 2b and 3b in Table 1, respectively, and the raw material 1a in Step 2 was replaced by the raw material 1i, and the following compounds were obtained:

(trans)-4-(3-(2-chloro-6-n-propyl-benzylidene)-4-fluoro-indolin-2-on-1-yl)-benzoic acid (20A)

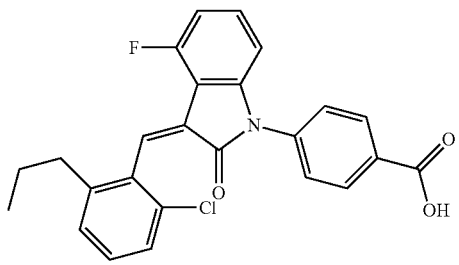 [SMILES: CCCc1cccc(Cl)c1/C=C1\C(=O)N(c2ccc(C(=O)O)cc2)c2cccc(F)c21]

Relevant characterization data are as follows: ESI-MS: [M+H]+=436.2

¹H-NMR (CDCl₃) δ: ppm 8.31 (d, J=8.4 Hz, 2H), 8.02 (s, 1H), 7.67 (d, J=8.7 Hz, 2H), 7.32-7.27 (m, 2H), 7.23-7.15 (m, 2H), 6.74 (d, J=7.8 Hz, 1H), 6.68-6.62 (m, 1H), 2.60 (t, 2H), 1.58 (m, 2H), 0.89 (t, 3H); and (cis)-4-(3-(2-chloro-6-n-propyl-benzylidene)-4-fluoro-indolin-2-on-1-yl)-benzoic acid (20B)

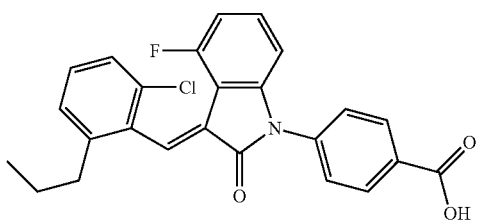 [SMILES: CCCc1cccc(Cl)c1/C=C1/C(=O)N(c2ccc(C(=O)O)cc2)c2cccc(F)c21]

Relevant characterization data are as follows: ESI-MS: [M+H]$^+$=436.2

$^1$H-NMR (CDCl$_3$) δ: ppm 8.20 (d, J=8.4 Hz, 2H), 7.94 (s, 1H), 7.56 (d, J=9.0 Hz, 2H), 7.30-7.27 (m, 2H), 7.25-7.17 (m, 2H), 6.93-6.88 (m, 1H), 6.79 (d, J=7.8 Hz, 1H), 2.63 (t, 2H), 1.60 (m, 2H), 0.91 (t, 3H).

Example 21

The preparation of the compound of this example was similar to the method described in Example 1, except that the raw material 2a in Step 1 was replaced by the raw material 2b in Table 1, and the following compounds were obtained:

(trans)-4-(3-(2-chloro-6-cyclopropyl-benzylidene)-4-fluoro-indolin-2-on-1-yl)-2-hydroxy-benzoic acid (21A)

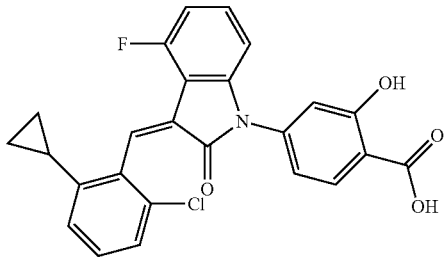 [SMILES: O=C(O)c1ccc(N2C(=O)/C(=C\c3c(Cl)cccc3C3CC3)c3c(F)cccc32)cc1O]

Relevant characterization data are as follows: ESI-MS: [M+H]$^+$=450.2

$^1$H-NMR (300 MHz, CD$_3$OD-d$_4$) δ: ppm 8.02 (m, 2H), 7.35 (m, 1H), 7.24 (m, 3H), 6.95 (m, 3H), 6.82 (d, 1H, J=8.1 Hz), 1.92 (m, 1H), 0.91 (m, 2H), 0.74 (m, 1H), 0.65 (m, 1H); and (cis)-4-(3-(2-chloro-6-cyclopropyl-benzylidene)-4-fluoro-indolin-2-on-1-yl)-2-hydroxy-benzoic acid (21B)

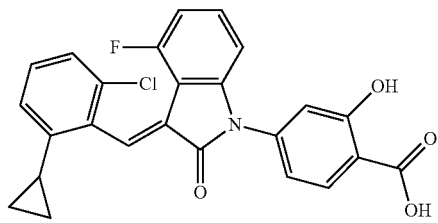 [SMILES: O=C(O)c1ccc(N2C(=O)/C(=C/c3c(Cl)cccc3C3CC3)c3c(F)cccc32)cc1O]

Relevant characterization data are as follows: ESI-MS: [M+H]$^+$=450.2

$^1$H-NMR (300 MHz, CD$_3$OD-d$_4$) δ: ppm 8.04 (d, 1H, J=8.4 Hz), 8.02 (s, 1H), 7.27 (m, 3H), 7.01-7.19 (m, 3H), 6.93 (m, 1H), 6.76 (d, 1H, J=7.8 Hz), 6.69 (s, 1H), 1.83 (m, 1H), 0.90 (m, 2H), 0.67 (m, 2H).

Example 22

The preparation of the compound of this example was similar to the method described in Example 1, except that the raw material 2a in Step 1 was replaced by the raw material 2b in Table 1, and the raw material 1a in Step 2 was replaced by the raw material 1b, and the following compounds were obtained:

(trans)-4-(3-(2,6-dichloro-benzylidene)-4-fluoro-indolin-2-on-1-yl)-2-hydroxy-benzoic acid (22A)

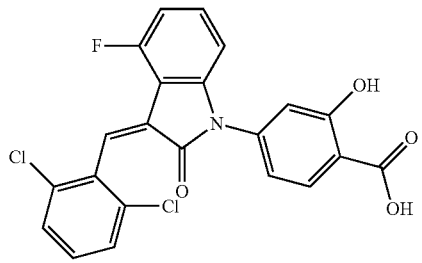 [SMILES: O=C(O)c1ccc(N2C(=O)/C(=C\c3c(Cl)cccc3Cl)c3c(F)cccc32)cc1O]

Relevant characterization data are as follows: ESI-MS: [M+H]$^+$=444.1

$^1$H-NMR (300 MHz, CD$_3$OD-d$_4$) δ: ppm 8.07 (d, 1H, J=8.4 Hz), 7.80 (s, 1H), 7.48 (m, 2H), 7.29-7.41 (m, 2H), 7.10 (s, 1H), 7.05 (d, 1H, J=8.4 Hz), 6.69-6.80 (m, 2H); and (cis)-4-(3-(2,6-dichloro-benzylidene)-4-fluoro-indolin-2-on-1-yl)-2-hydroxy-benzoic acid (22B)

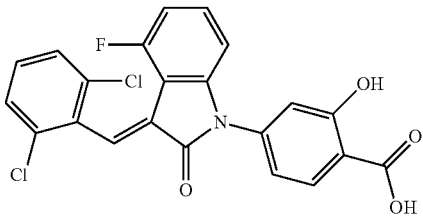

Relevant characterization data are as follows: ESI-MS: [M+H]$^+$=444.1

$^1$H-NMR (300 MHz, CD$_3$OD-d$_4$) δ: ppm 8.01 (d, 1H, J=8.4 Hz), 7.76 (s, 1H), 7.44 (m, 2H), 7.35 (m, 2H), 6.97 (m, 3H), 6.82 (d, 1H, J=7.8 Hz).

Example 23

The preparation of the compound of this example was similar to the method described in Example 1, except that the raw materials 2a and 3a in Step 1 were replaced by the raw materials 2c and 3b in Table 1, respectively, and the raw material 1a in Step 2 was replaced by the raw material 1b, and (trans)-4-(3-(2,6-dichloro-benzylidene)-4-chloro-indolin-2-on-1-yl)-benzoic acid was obtained.

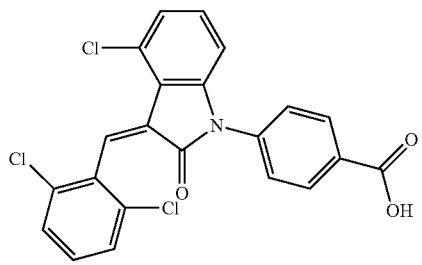 [SMILES: O=C(O)c1ccc(N2C(=O)/C(=C\c3c(Cl)cccc3Cl)c3c(Cl)cccc32)cc1]

Relevant characterization data are as follows: ESI-MS: [M+H]⁺=446.1

¹H-NMR (300 MHz, DMSO-d₆) δ: ppm 12.99 (brs, 1H), 8.31-7.78 (m, 3H), 7.70-7.52 (m, 4H), 7.43-7.26 (m, 3H), 6.91-6.81 (m, 1H).

Example 24

The preparation of the compound of this example was similar to the method described in Example 1, except that the raw material 3a in Step 1 was replaced by the raw material 3c in Table 1, and (trans)-4-(3-(2-chloro-6-cyclopropyl-benzylidene)-4-methylindolin-2-on-1-yl)-2-chlorobenzoic acid was obtained.

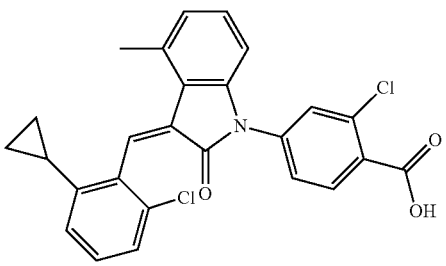

Relevant characterization data are as follows: ESI-MS: [M+H]⁺=464.3

¹H-NMR (300 MHz, DMSO-d₆) δ: ppm 8.01-7.79 (m, 2H), 7.64-7.62 (m, 1H), 7.54-7.49 (m, 1H), 7.35-7.22 (m, 3H), 7.05-6.93 (m, 2H), 6.86-6.71 (m, 1H), 1.76-1.71 (m, 1H), 1.26 (s, 3H), 0.87-0.83 (m, 2H), 0.71-0.63 (m, 2H).

Example 25

The preparation of the compound of this example was similar to the method described in Example 1, except that the raw material 3a in Step 1 was replaced by the raw material 3d in Table 1, and (trans)-4-(3-(2-chloro-6-cyclopropyl-benzylidene)-4-methylindolin-2-on-1-yl)-2-fluorobenzoic acid was obtained.

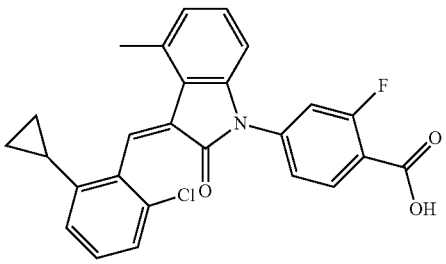 [SMILES: Cc1cccc2c1/C(=C/c1c(Cl)cccc1C1CC1)C(=O)N2c1ccc(C(=O)O)c(F)c1]

Relevant characterization data are as follows: ESI-MS: [M+H]⁺=448.9

¹H-NMR (300 MHz, DMSO-d₆) δ: ppm 8.03 (t, 1H, J=8.1 Hz), 7.89 (s, 1H), 7.38-7.46 (m, 2H), 7.22-7.36 (m, 3H), 7.01 (dd, 2H, J=7.5, 18.3 Hz), 6.86 (d, 1H, J=7.8 Hz), 2.64 (s, 3H), 0.83-0.87 (m, 3H), 0.63-0.70 (m, 2H).

Example 26

The preparation of the compound of this example was similar to the method described in Example 1, except that the raw material 2a in Step 1 was replaced by the raw material 2g in Table 1, and (trans)-4-(3-(2-chloro-6-bromobenzylidene)-4-trifluoromethyl indolin-2-on-1-yl)-2-hydroxybenzolic acid was obtained.

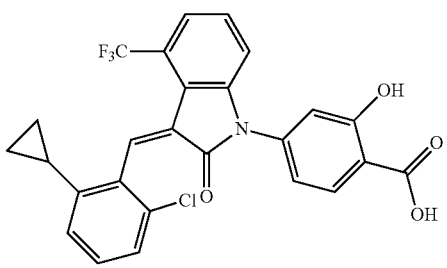 [SMILES: O=C(O)c1ccc(N2C(=O)/C(=C\c3c(Cl)cccc3C3CC3)c3c2cccc3C(F)(F)F)cc1O]

Relevant characterization data are as follows: ESI-MS: [M+H]⁺=500.3

¹H-NMR (300 MHz, DMSO-d₆) δ: ppm 11.71 (brs, 1H), 7.98 (S, 1H), 7.90-7.82 (m, 1H), 7.57-7.48 (m, 2H), 7.35-7.25 (m, 2H), 7.19-7.10 (m, 1H), 7.03-6.73 (m, 3H), 5.36 (s, 1H), 1.78-1.73 (m, 1H), 1.49-1.46 (m, 2H), 0.83-0.86 (m, 2H).

Example 27

The preparation of the compound of this example was similar to the method described in Example 1, except that the raw material 2a in Step 1 was replaced by the raw material 2h in Table 1, and (trans)-4-(3-(2-chloro-6-bromo-benzylidene)-indolin-2-on-1-yl)-2-hydroxybenzolic acid was obtained.

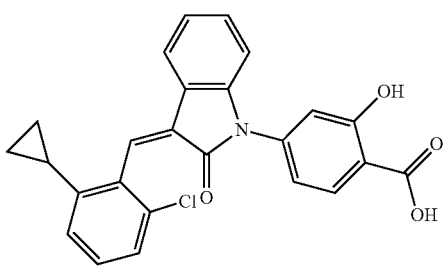 [SMILES: O=C(O)c1ccc(N2C(=O)/C(=C\c3c(Cl)cccc3C3CC3)c3ccccc32)cc1O]

Relevant characterization data are as follows: ESI-MS: [M+H]⁺=432.0

¹H-NMR (300 MHz, CDCl₃) δ: ppm 7.98-8.09 (m, 2H), 7.31-7.37 (m, 2H), 7.10-7.24 (m, 3H), 6.89-6.99 (m, 3H), 6.82-6.84 (m, 1H), 1.89-2.00 (m, 1H), 0.85-0.94 (m, 3H), 0.64-0.76 (m, 1H).

Example 28: (trans)-4-(3-(2-chloro-6-bromo-benzylidene)-indolin-2-on-1-yl)-2-pivaloyloxybenzoic acid

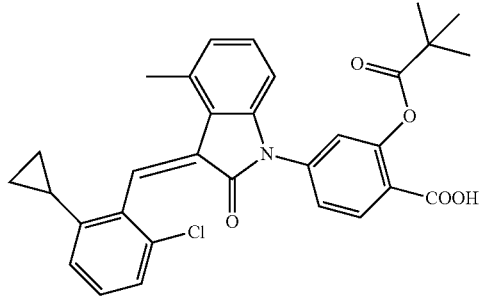 [SMILES: Cc1cccc2c1/C(=C/c1c(Cl)cccc1C1CC1)C(=O)N2c1ccc(C(=O)O)c(OC(=O)C(C)(C)C)c1]

Relevant characterization data are as follows: ESI-MS: [M+H]$^+$=530.1

$^1$H-NMR (300 MHz, CDCl$_3$) δ: ppm 8.18 (d, 2H, J=8.4 Hz), 7.81 (s, 1H), 7.43 (dd, 1H, J=8.7 Hz, J=1.8 Hz), 7.16-7.28 (m, 5H), 6.90-7.00 (m, 3H), 2.69 (s, 3H), 1.90-1.95 (m, 1H), 1.35 (s, 9H), 0.80-0.90 (m, 3H), 0.52-0.60 (m, 1H).

Example 29

The preparation of the compound of this example was similar to the method described in Example 1, except that the raw material 1a in Step 2 was replaced by the raw material 1h in Table 1, and the raw material 3a in Step 3 was replaced by the raw material 3b, and (trans)-4-(3-(2-chloro-6-methyl-benzylidene)-4-methylindolin-2-on-1-yl)-benzoic acid was obtained.

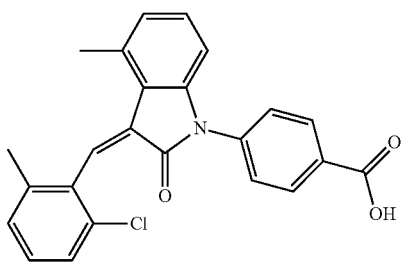 [SMILES: Cc1cccc(Cl)c1/C=C1\C(=O)N(c2ccc(C(=O)O)cc2)c2cccc(C)c21]

Relevant characterization data are as follows: ESI-MS: [M+H]$^+$=404.2

$^1$H-NMR (300 MHz, CDCl$_3$) δ: ppm 8.19 (d, J=8.4 Hz, 2H), 7.72 (s, 1H), 7.56 (d, J=8.4 Hz, 2H), 7.27-7.15 (m, 4H), 6.98 (d, J=7.8 Hz, 1H), 6.84 (d, J=7.5 Hz, 1H), 2.69 (s, 3H), 2.34 (s, 3H).

Example 30

The preparation of the compound of this example was similar to the method described in Example 1, except that the raw material 2a in Step 1 was replaced by the raw material 2d in Table 1, and the raw material 3a in Step 3 was replaced by the raw material 3b, and (trans)-4-(3-(2-chloro-6-methyl-benzylidene)-4-methoxyindolin-2-on-1-yl)-benzoic acid was obtained.

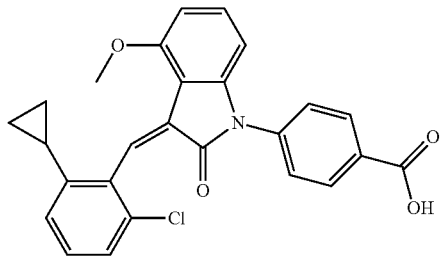 [SMILES: COc1cccc2c1/C(=C/c1c(Cl)cccc1C1CC1)C(=O)N2c1ccc(C(=O)O)cc1]

Relevant characterization data are as follows: ESI-MS: [M+H]$^+$=446.2

$^1$H-NMR (300 MHz, DMSO-d$_6$) δ: ppm 13.06 (brs, 1H), 8.08-8.06 (m, 3H), 7.55-7.52 (d, 2H), 7.35-7.21 (m, 3H), 6.94-6.90 (s, 2H), 6.58-6.55 (d, 1H), 4.02 (s, 3H), 1.93-1.87 (m, 1H), 0.90-0.84 (m, 2H), 0.73-0.67 (m, 1H), 0.64-0.58 (m, 1H).

Example 31

The preparation of the compound of this example was similar to the method described in Example 1, except that the raw material 1a in Step 2 was replaced by the raw material 1b in Table 1, and the raw material 3a in Step 3 was replaced by the raw material 3b, and (trans)-4-(3-(2,6-dichloro-benzylidene)-4-methoxyindolin-2-on-1-yl)-benzoic acid was obtained.

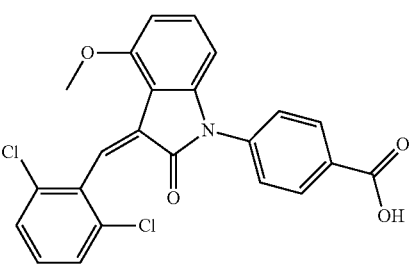 [SMILES: COc1cccc2c1/C(=C/c1c(Cl)cccc1Cl)C(=O)N2c1ccc(C(=O)O)cc1]

Relevant characterization data are as follows: ESI-MS: [M+H]$^+$=440.2

$^1$H-NMR (300 MHz, DMSO-d$_6$) δ: ppm 12.99 (s, 1H), 8.11 (m, 2H), 7.84 (s, 1H), 7.69-7.51 (m, 4H), 7.33 (m, 2H), 6.93 (d, J=8.4 Hz, 1H), 6.56 (d, J=7.8 Hz, 1H), 4.03 (s, 3H).

Example 32

The preparation of the compound of this example was similar to the method described in Example 1, except that the raw material aa in Step 2 was replaced by the raw material 1f in Table 1, and the raw material 3a in Step 3 was replaced by the raw material 3b, and (trans)-4-(3-(2-chloro-6-methoxy-benzylidene)-4-methylindolin-2-on-1-yl)-benzoic acid was obtained.

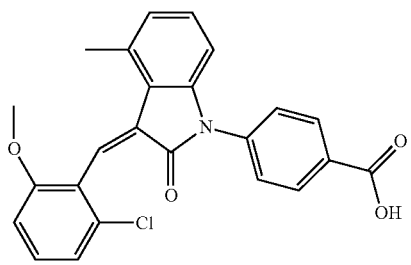 [SMILES: COc1cccc(Cl)c1/C=C1\C(=O)N(c2ccc(C(=O)O)cc2)c2cccc(C)c21]

Relevant characterization data are as follows: ESI-MS: [M+H]⁺=420.2

¹H-NMR (300 MHz, CDCl₃) δ: ppm 8.18 (d, J=8.4 Hz, 2H), 8.61 (s, 1H), 7.56 (d, J=8.4 Hz, 2H), 7.24-7.14 (m, 2H), 7.05 (d, J=7.5 Hz, 1H), 6.96 (d, J=7.8 Hz, 1H), 6.85-6.79 (m, 2H), 3.81 (s, 3H), 2.68 (s, 3H).

Example 33

The preparation of the compound of this example was similar to the method described in Example 1, except that the raw material 3a in Step 3 was replaced by the raw material 3e, and (trans)-4-(3-(2-chloro-6-methoxy-benzylidene)-4-methylindolin-2-on-1-yl)-2-aminobenzoic acid was obtained.

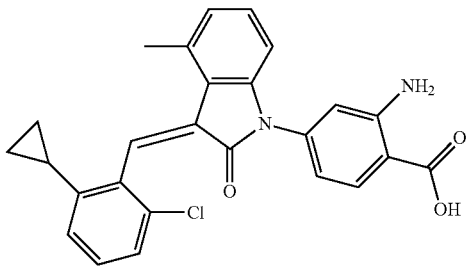 [SMILES: Cc1cccc2c1/C(=C/c1c(Cl)cccc1C1CC1)C(=O)N2c1ccc(C(=O)O)c(N)c1]

Relevant characterization data are as follows: ESI-MS: [M+H]⁺=445.3

¹H-NMR (300 MHz, DMSO-d₆) δ: ppm 7.85-7.78 (m, 2H), 7.31-7.21 (m, 3H), 7.01-6.96 (m, 2H), 6.79-6.77 (m, 2H), 6.52-6.48 (m, 1H), 2.63 (s, 3H), 1.95-1.89 (m, 1H), 0.87-0.83 (m, 2H), 0.69-0.63 (m, 2H).

Example 34

The preparation of the compound of this example was similar to the method described in Example 1, except that the raw material 1a in Step 2 was replaced by the raw material 1j in Table 1, and the raw material 3a in Step 3 was replaced by the raw material 3b, and (trans)-4-(3-(2-chloro-6-cyclohexyl-benzylidene)-4-methylindolin-2-on-1-yl)-benzoic acid was obtained.

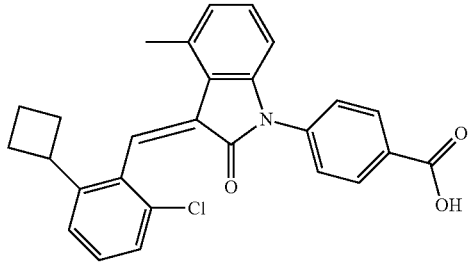 [SMILES: Cc1cccc2c1/C(=C/c1c(Cl)cccc1C1CCC1)C(=O)N2c1ccc(C(=O)O)cc1]

Relevant characterization data are as follows: ESI-MS: [M+H]⁺=444.2

¹H-NMR (300 MHz, DMSO-d₆) δ: ppm 12.94 (brs, 1H), 8.08-8.05 (d, 2H), 7.77 (s, 1H), 7.54-7.51 (d, 2H), 7.34-7.22 (m, 4H), 7.04-7.02 (d, 1H), 6.79-6.76 (d, 1H), 3.65-3.57 (m, 1H), 2.62 (s, 3H), 2.22-1.99 (m, 4H), 1.92-1.70 (m, 2H).

Example 35

The preparation of the compound of this example was similar to the method described in Example 1, except that the raw material 1a in Step 2 was replaced by the raw material 1j in Table 1, and (trans)-4-(3-(2-chloro-6-cyclohexyl-benzylidene)-4-methylindolin-2-on-1-yl)-2-hydroxybenzolic acid was obtained.

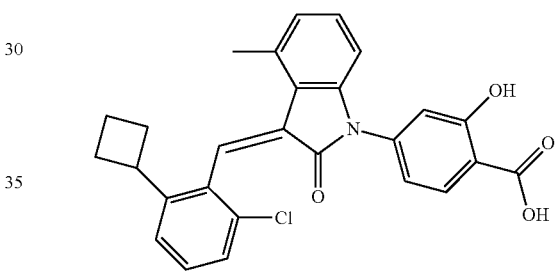

Relevant characterization data are as follows: ESI-MS: [M+H]⁺=460.3

¹H-NMR (300 MHz, DMSO-d₆) δ: ppm 7.91-7.89 (d, 1H), 7.76 (s, 1H), 7.32-7.23 (m, 4H), 7.04-6.93 (m, 3H), 6.82-6.80 (d, 1H), 3.62-3.59 (m, 1H), 2.62 (s, 3H), 2.21-1.99 (m, 4H), 1.92-1.70 (m, 2H).

Example 36

The preparation of the compound of this example was similar to the method described in Example 1, except that the raw material 1a in Step 2 was replaced by the raw material 1k in Table 1, and (trans)-4-(3-(2-chloro-6-isopropyl-benzylidene)-4-methylindolin-2-on-1-yl)-2-hydroxybenzolic acid was obtained.

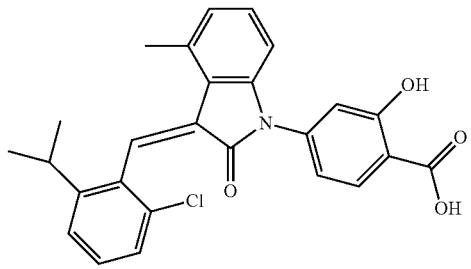 [SMILES: Cc1cccc2c1/C(=C/c1c(Cl)cccc1C(C)C)C(=O)N2c1ccc(C(=O)O)c(O)c1]

Relevant characterization data are as follows: ESI-MS: [M+H]$^+$=448.3

$^1$H-NMR (300 MHz, CDCl$_3$) δ: ppm 7.96 (d, 1H, J=8.4 Hz), 7.75 (s, 1H), 7.16-7.31 (m, 4H), 7.09 (s, 1H), 7.00 (d, 2H, J=8.4 Hz), 6.91 (d, 1H, J=8.4 Hz), 3.29 (m, 2H), 2.61 (s, 3H), 1.15 (t, J=7.5 Hz, 3H).

Example 37

The preparation of the compound of this example was similar to the method described in Example 1, except that the raw material 1a in Step 2 was replaced by the raw material 1l in Table 1, and (trans)-4-(3-(2-chloro-6-ethyl-benzylidene)-4-methylindolin-2-on-1-yl)-2-hydroxybenzolic acid was obtained.

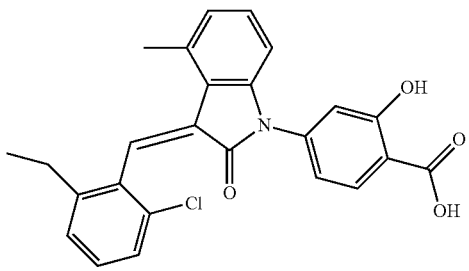 [SMILES: CCc1cccc(Cl)c1/C=C1\C(=O)N(c2ccc(C(=O)O)c(O)c2)c2cccc(C)c21]

Relevant characterization data are as follows: ESI-MS: [M+H]$^+$=434.3

$^1$H-NMR (300 MHz, CD$_3$OD) δ: ppm 7.99 (d, 1H, J=8.4 Hz), 7.81 (s, 1H), 7.19-7.27 (m, 4H), 6.99 (d, 1H, J=8.4 Hz), 6.89-6.94 (m, 2H), 6.78 (d, 1H, J=7.8 Hz), 2.69 (s, 3H), 2.02 (s, 3H).

Test of the Biological Activities of the Compounds of the Present Application

1. Screening of In Vitro Biological Activities: TR-FRET Screening

The compounds of the present application can regulate (inhibit) the biological activity of the nuclear receptor RORγ, and the intensity of such a regulation (inhibition) can be evaluated by TR-FRET (Time-Resolved Fluorescence Resonance Energy Transfer) screening system. Nuclear receptor cofactors (co-activators and co-repressors) can regulate the transcription of target genes through interactions with nuclear receptors. If a ligand (test compound) interferes with the interaction between a nuclear receptor and a cofactor, such a ligand (test compound) can regulate the transcription of the corresponding gene.

The method employs LanthaScreen TR-FRET (Time-Resolved Fluorescence Resonance Energy Transfer) technique of Life Technologies Co. to test the compounds for their abilities to regulate (agonize or inversely agonize) the interaction between RORγ and its co-activator. RORγ-LBD is indirectly labeled by binding a terbium(Tb)-labeled anti-GST antibody (Life Technologies #PV3550) onto the GST tag of RORγ-LBD (Life Technologies #PV5887). When no ligand is present, RORγ can continuously bind to a fluorescein-labeled co-activator, and the binding of an agonist to RORγ can enhance the interaction between RORγ and the fluorescein-labeled co-activator; while the binding of an inverse agonist to RORγ can inhibit the interaction between RORγ and the fluorescein-labeled co-activator. When the fluorescein-labeled co-activator and the terbium-labeled anti-GST antibody-RORγ-LBD composite are close to each other to a certain distance, an energy transfer can occur, generating a TR-FRET signal. The co-activators employed in the method are not limited to D22 (Life Technologies #PV4386).

(1) The final concentrations in the reaction system and the reaction conditions in the method are shown in the table below:

TABLE 2

| Concentration of RORγ-LBD | Fluorescein-labeled co-activator | Concentration of activator peptide | Concentration of Tb-labeled anti-GST antibody | Total volume (μL) | Reaction conditions |
|---|---|---|---|---|---|
| 2 nM | D22 | 150 nM Fluorescein-D22 | 2 nM | 20 | 22° C., 5 hr |

(2) Experiments

Preparation of Complete TR-FRET Coregulator Buffer D (hereinbelow referred to as Complete Buffer D): adding DTT (Life Technologies #P2325) to TR-FRET Coregulator Buffer D (Life Technologies #PV4420) until the DTT final concentration is 5 mM.

A mixed solution of 2× Fluorescein-D22 (0.3 μM, referring to Table 2 when using other co-activating peptides) and 2× Tb-labeled anti-GST antibody (4 nM) was prepared using Complete Buffer D, and was added to a 384-well plate (Corning 3376) at 10 μL/well.

Gradient diluted solutions of the test compounds having 100× final concentrations were prepared with DMSO. Then, the test compounds were 4× diluted with Complete Buffer D (DMSO content: 4%), and were added to a 384-well plate at 5 μL/well, and mixed uniformly. To a positive control well was added Complete Buffer D (no test compound) containing 4% DMSO at 5 μL/well.

4× solution of RORγ-LBD (8 nM) was prepared with Complete Buffer D, and was added to a 384-well plate at 5 μL/well, and mixed uniformly. To a negative control well was added Complete Buffer D (no RORγ-LBD) at 5 μL/well. The 384-well plate was placed in a thermostatic oscillator, and was incubated in a dark place at 23° C. for 4-5 hours.

The fluorescence intensity was determined with Tecan M1000 Pro (manufacturer: Tecan): 1) excitation wavelength: 332/20 nm, emission wavelength: 490/10 nm, gain value: optimized, flash: model 2 (100 Hz), delay time: 100 µs, integration time: 200 µs; 2) excitation wavelength: 332/20 nm, emission wavelength: 520/20 nm, gain value: optimized, flash: model 2 (100 Hz), delay time: 100 µs, integration time: 200 µs.

(3) Data analysis

A logarithm curve of TR-FRET ratio F520/F490—compound concentration was plotted using GraphPad Prism program, and the $IC_{50}$ value was calculated. A lower value represents a stronger regulating (inhibiting) effect of the compound on the receptor RORγ.

The $IC_{50}$ values of the effects of the compounds of the present application on RORγ are shown in the following table:

TABLE 3

| Compounds in Examples | $IC_{50}$ Values (nM) |
|---|---|
| 1 | +++ |
| 2A | +++ |
| 2B | ++ |
| 3 | +++ |
| 4 | +++ |
| 5 | +++ |
| 6 | +++ |
| 7 | +++ |
| 8 | +++ |
| 9 | +++ |
| 10 | +++ |
| 11 | ++ |
| 12 | +++ |
| 13 | ++ |
| 14 | ++ |
| 15A | +++ |
| 15B | +++ |
| 16A | +++ |
| 16B | +++ |
| 17A | ++ |
| 17B | ++ |
| 18A | + |
| 18B | + |
| 19A | +++ |
| 19B | +++ |
| 20A | ++ |
| 20B | ++ |
| 21A | +++ |
| 21B | ++ |
| 22A | +++ |
| 22B | +++ |
| 23 | +++ |
| 24 | ++ |
| 25 | ++ |
| 26 | ++ |
| 27 | + |
| 28 | ++ |
| 29 | ++ |
| 30 | +++ |
| 31 | + |
| 32 | + |
| 33 | + |
| 34 | +++ |
| 35 | ++ |
| 36 | +++ |
| 37 | +++ |

In Table 3, "+" represents an $IC_{50}$ value of "1000-10000", "++" represents an $IC_{50}$ value of "100-1000", and "+++" represents an $IC_{50}$ value of "<100".

2. Cell Experiments: Differentiation Inhibition Experiments on Th17 Cells

5 µg/mL mouse CD3 antibody (purchased from BD) was coated on a 96-well plate (37° C., 2-6 hours) and stored for future use. C57 mouse lymph gland naïve CD4 positive T cells were separated using CD4+ T cell isolation kit II (purchased from MACS), and were inoculated to the coated 96-well plate at $5×10^5$ cells/well/100 µL. The test sample was gradient diluted with RMPI-1640 culture medium (Gibco, 22440), and was made to be 4 times of the final concentration (starting from 1 µM, 10 times dilution, setting 6 drug concentrations). The diluted test sample was added at 50 µL/well to the test well inoculated with cells. To each of the positive and negative control wells was added 50 µL RMPI-1640 culture medium. To each of the test wells and the positive control wells was further added 50 µL mixed solution of activators (20 ug/mL mouse CD28 antibody (purchased from BD); 40 ug/mL mouse IL-4 antibody (purchased from BD); 40 ug/mL mouse IFNγ antibody (purchased from BD); 4 ng/mL mouse TGF-β1 (purchased from R&D); 200 ng/mL mouse IL-6 (purchased from R&D); 20 ng/mL mouse IL-23 (purchased from R&D)) having a 4-fold final concentration; to the negative control well was added 50 µL RMPI-1640 culture medium. The loaded 96-well plate was placed in an incubator at 37° C., 5% $CO_2$ and was cultured for 66 hours, followed by adding to each well 50 uL mixed solution of PMA (purchased from Sigma, working concentration: 50 ng/mL) and Ionomycin (purchased from Sigma, working concentration: 1 ug/mL), and culturing at 37° C. for another 6 hours. After the culture was completed, a cell culture supernatant was taken, and the IL-17A content in the supernatant was determined using mouse IL-17A ELISA kit (purchased from Dakewe), and the inhibition rate and the $IC_{50}$ value were calculated. The specific operation followed the kit specification (see below):

(1) Determining the number of required strips according to the number of the test wells (blank and standard); taking out the Washing buffer (50×) and the ready-to-use solution from the kit 20 min in advance to balance to room temperature.

(2) Loading samples: adding diluted Cytokine standard to the standard well at 100 µL/well, adding the sample to the sample well at 100 µL/well, setting a blank well, in which Dilution buffer R (1×) was used instead of the sample and the standard.

(3) Adding testing antibody: adding diluted Biotinylated antibody at 50 µL/well; covering with a sealing film after mixing uniformly, and incubating at 37° C. for 90 min.

(4) Washing the plate: deducting the liquid in the well, adding 1× washing buffer at 300 µL/well; maintain for 1 min, then discarding the liquid in the well; repeating 4 times, each time deducting to dryness on filter pater.

(5) Adding enzyme: adding diluted Streptavidin-HRP at 100 µL/well; covering with a sealing film, and incubating at 37° C. for 30 min.

(6) Washing the plate: repeating Step 5.

(7) Color development: adding TMB at 100 µL/well, incubating at 37° C. in a dark place for 5-30 min, and determining to terminate the reaction according to the depth of the color in the well (dark blue). Normally, a good effect can be achieved by color development for 10-20 min.

(8) Terminating the reaction: rapidly adding a stop solution at 100 µL/well to terminate the reaction.

Reading the plate: 10 min after termination, reading the value using a measurement wavelength of 450 nm.

The inhibition activity (inhibition rate) of some compounds of the present application on the differentiation of Th17 cells are shown in the following table:

TABLE 4

| Compounds of Examples | Inhibition Rate (1 µM) |
|---|---|
| 1 | >50% |
| 2A | >50% |
| 3 | >50% |

TABLE 4-continued

| Compounds of Examples | Inhibition Rate (1 μM) |
|---|---|
| 4 | >50% |
| 10 | >50% |
| 15A | >50% |
| 15B | <50% |
| 16B | >50% |

3. Experiments on In Vivo Activity in Rat Anti-Arthritis Model CIA

Test animals: female wistar rats, individual body weight ranging from 180 to 220 g.

Experiments:

(1) Bovine type II collagen (CII, 2 mg/ml, Chondrex, 20022) and incomplete Freud's adjuvant (IFA, Sigma-Aldrich) were mixed in 1:1 equal volume, and sufficiently emulsified in an ice bath to give an emulsion in which the final concentration of CII was 1 mg/ml.

(2) Each rat was intradermally injected at the tail root with 200 ul of emulsion to conduct a primary immunization. 7 days after the primary immunization, each rat was intradermally injected at the tail root with 100 ul of the emulsion to conduct a booster immunization.

(3) Administration: Beginning from the 12$^{th}$ day after the primary immunization, test compounds (the compound of Example 1 and compound 2A of Example 2 of the present invention) were intragastrically administered to the rat twice a day. After the administration, the lesion degrees of the limb joints of the rats were observed and recorded once every 2 days. The solvent was dimethyl sulfoxide/Tween 80/PEG400/deionized water=1/5/20/74.

Scoring standards: The systematic lesion was evaluated according to a 5-grade scoring method, and the arthritis index (severity score) was calculated according to the total score of the lesion degrees of the 4 limbs. The standards are as follows: 0, no redness and swelling; 1, redness and swelling at the ankle joint or the tarsal joint; 2, swelling at from the ankle joint to the tarsal joint; 3, swelling at from the ankle joint to the metatarsal joint; 4, swelling at all the paws and joints, including the ankle joint.

Results: The in vivo activities of the compounds of the present application and the solvent in the rat anti-arthritis CIA model are shown in FIG. 1. A lower arthritis index (severity score) represents a stronger therapeutic and relieving effect on the lesion and a better in vivo activity of the compound.

The above invention has been described in detail by way of illustration and Examples for the purpose of explanation and understanding. It will be apparent to those skilled in the art that modifications and improvements may be made within the scope of the appended claims. Accordingly, it is to be understood that the above description is illustrative rather than restrictive. Therefore, the scope of the present application includes the whole scope of the appended claims and the equivalents of the claims.

The invention claimed is:

1. A compound, or a stereoisomer, a tautomer, a pharmaceutically acceptable salt, or a solvate thereof, the compound having structural formula (I):

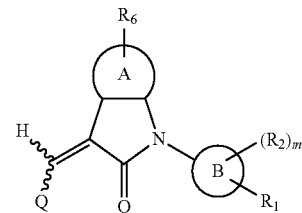

(I)

wherein:
A is 5- or 6-membered aryl or heteroaryl, wherein the heteroaryl group has one or more heteroatoms selected from the group consisting of N, O and S;
$R_6$ is selected from one or more of the following groups: hydrogen, alkyl, cycloalkyl, alkoxy, aryl, halogen, trifluoromethyl, amino, cyano, hydroxyl, carboxyl, halogenated alkyl, halogenated alkoxy, alkylamino, dialkylamino, alkylsulfonyl, aminosulfonyl, sulfonamido, amido, carbonyl, alkylaminocarbonyl or dialkylaminocarbonyl;
B is aryl or heteroaryl, wherein the heteroaryl group has one or more heteroatoms selected from the group consisting of N, O and S;
Q is aryl or heteroaryl, which is optionally substituted by one or more of the following groups: halogen, trifluoromethyl, alkyl, cycloalkyl, alkoxy, hydroxyl, amino, cyano, nitro, carbonyl, aryl, heteroaryl, alkylamino, dialkylamino, alkylaminocarbonyl, dialkylaminocarbonyl, alkylsulfonyl and alkylcarbonyl, wherein the alkyl, cycloalkyl, alkoxy, aryl or heteroaryl group may be optionally substituted by one or more halogens;
$R_1$ is selected from the group consisting of —C(=O)OH, —C(=O)O-alkyl, amido, 5-tetrazole, $HOC(CF_3)_2$, phosphoric acid group, phosphate ester group, cyano, alkylaminocarbonyl, sulfonamido and alkylsulfonyl;
$R_2$ is selected from the group consisting of hydrogen, hydroxyl, halogen, mercapto, amino, cyano, nitro, $(C_{1-4})$alkyl, $(C_{1-4})$alkoxy and $(C_{1-4})$alkylC(=O)O—, wherein the $(C_{1-4})$alkyl or $(C_{1-4})$alkoxy group may be optionally substituted by one or more halogens; and
m is 0, 1, 2, 3 or 4.

2. The compound of claim 1, or a stereoisomer, a tautomer, a pharmaceutically acceptable salt, or a solvate thereof, the compound having structural formula (Ia):

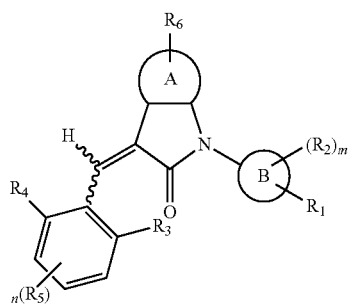

(Ia)

wherein:
A, B, $R_1$ and $R_2$ are as defined in claim 1;
$R_3$, $R_4$ and $R_5$ are independently selected from the group consisting of H, halogen, trifluoromethyl, alkyl, cycloalkyl, alkoxy, hydroxyl, amino, cyano, aryl, heteroaryl, alkylamino, dialkylamino, alkylsulfonyl and alkylcarbonyl;
m is 0, 1, 2, 3 or 4; and
n is 0, 1, 2 or 3.

3. The compound of claim 2, or a stereoisomer, a tautomer, a pharmaceutically acceptable salt, or a solvate thereof, the compound having structural formula (Ib):

(Ib)

wherein:
A is phenyl, pyridyl, thienyl, furanyl or pyrimidinyl, and $R_1$, $R_2$, $R_3$, $R_4$, $R_5$ and $R_6$ are as defined in claim 2.

4. The compound of claim 3, or a stereoisomer, a tautomer, a pharmaceutically acceptable salt, or a solvate thereof, the compound having structural formula (Ic)

(Ic)

wherein:
$R_1$ is selected from the group consisting of —C(=O)OH, —C(=O)O-alkyl, amido, 5-tetrazole, $HOC(CF_3)_2$, phosphoric acid group, phosphate ester group, cyano, alkylaminocarbonyl, sulfonamido and alkylsulfonyl;
$R_2$ is selected from the group consisting of hydrogen, hydroxyl, amino, mercapto, halogen, cyano, nitro, $(C_{1-4})$alkyl, $(C_{1-4})$alkoxy and $(C_{1-3})$alkylC(=O)O—, wherein the $(C_{1-4})$alkyl or $(C_{1-4})$alkoxy group may be optionally substituted by one or more halogens;
$R_3$, $R_4$ and $R_5$ may be independently selected from the group consisting of H, halogen, trifluoromethyl, alkyl, cycloalkyl, alkoxy, hydroxyl, amino, cyano, aryl, heteroaryl, alkylamino, dialkylamino, alkylsulfonyl and alkylcarbonyl; and
$R_6$ is selected from the group consisting of hydrogen, halogen, trifluoromethyl, alkyl, cycloalkyl, alkoxy, aryl, hydroxyl, amino, cyano and carbonyl.

5. The compound of claim 4, wherein, in formula (Ic), $R_1$ is —C(=O)OH, —C(=O)$NH_2$, —C(=O)O—$C_{1-6}$alkyl, —C(=O)NHR, —C(=O)N($R^a$)R wherein R and $R^a$ both are selected from $C_{1-6}$ alkyl, 5-tetrazole, $HOC(CF_3)_2$, phosphoric acid group, phosphate ester group, cyano, sulfonamido or $C_{1-6}$alkylsulfonyl;
$R_2$ is selected from the group consisting of hydrogen, hydroxyl, halogen, mercapto and amino;
$R_3$ is selected from the group consisting of halogen, amino, $C_{1-6}$alkylamino, di-$C_{1-6}$alkylamino, $C_{1-6}$alkylsulfonyl and $C_{1-6}$alkylcarbonyl;
$R_4$ is selected from the group consisting of H, halogen, trifluoromethyl, $C_{1-6}$alkyl, $C_{3-6}$cycloalkyl and $C_{1-6}$alkoxy,
$R_5$ is selected from the group consisting of H, $C_{1-6}$alkyl, $C_{3-6}$cycloalkyl and $C_{1-6}$alkoxy; and
$R_6$ is selected from the group consisting of halogen, trifluoromethyl, $C_{1-6}$alkyl, $C_{3-6}$cycloalkyl, $C_{1-6}$alkoxy and $C_{5-10}$aryl.

6. The compound of claim 1, wherein the compound is represented by (Id):

(Id)

wherein,
$R_2$ is selected from the group consisting of hydrogen, hydroxyl, halogen, amino, $(C_{1-4})$alkyl, $(C_{1-4})$alkoxy and $(C_{1-4})$alkylC(=O)O—, wherein the $(C_{1-4})$alkyl or $(C_{1-4})$alkoxy group may be optionally substituted by one or more halogens;
$R_6$ is selected from the following groups: hydrogen, halogen, trifluoromethyl, $(C_{1-4})$alkyl, $(C_{1-4})$alkoxy, $(C_{3-4})$cycloalkyl and $C_{5-10}$aryl; and
$R_3$ and $R_4$ are independently selected from the group consisting of halogen, trifluoromethyl, $(C_{1-4})$alkyl, $(C_{1-4})$alkoxy and $(C_{3-4})$cycloalkyl.

7. The compound of claim 6, wherein:
$R_2$ is optionally selected from the group consisting of hydrogen, hydroxyl, halogen, amino, $(C_{1-4})$alkyl, $(C_{1-4})$alkoxy and $(C_{1-4})$alkylC(=O)O—, wherein the $(C_{1-4})$alkyl or $(C_{1-4})$alkoxy group may be optionally substituted by one or more halogen atoms;
$R_6$ is selected from the following groups: hydrogen, halogen, trifluoromethyl, $(C_{1-4})$alkyl, $(C_{1-4})$alkoxy, $(C_{3-4})$cycloalkyl and $C_{5-10}$aryl;
$R_3$ is selected from halogen; and
$R_4$ is selected from the group consisting of halogen, trifluoromethyl, $(C_{1-4})$alkyl, $(C_{1-4})$alkoxy and $(C_{3-4})$cycloalkyl.

8. The compound of claim 6, wherein:
$R_2$ is hydrogen, hydroxyl or halogen; and
$R_6$ is fluoro, methyl, trifluoromethyl or methoxy.

9. The compound of claim 8, wherein:
$R_2$ is hydroxyl;
$R_6$ is fluoro, methyl or methoxy.

10. The compound of claim 2, wherein $R_3$ is chloro.

11. The compound of claim 10, wherein:
$R_2$ is hydroxyl;
$R_6$ is methyl;
$R_3$ is chloro; and
$R_4$ is cyclopropyl, trifluoromethyl or chloro.

12. The compound of claim 1, or a stereoisomer, a tautomer, a pharmaceutically acceptable salt, or a solvate thereof, the compound being selected from the group consisting of:
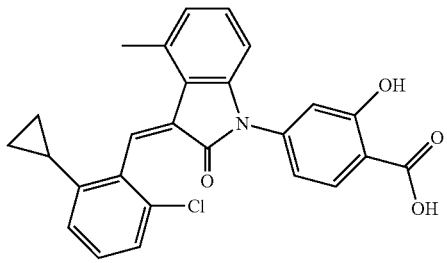
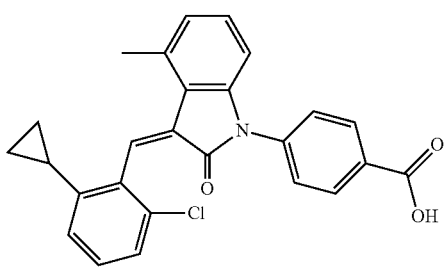
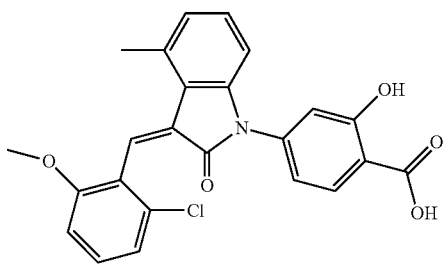
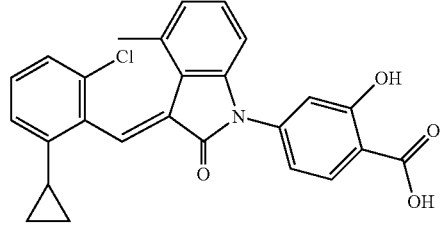
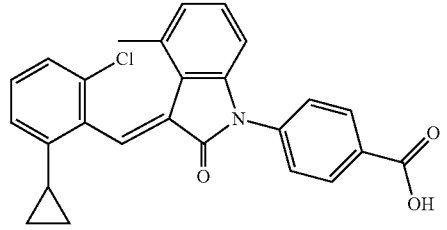
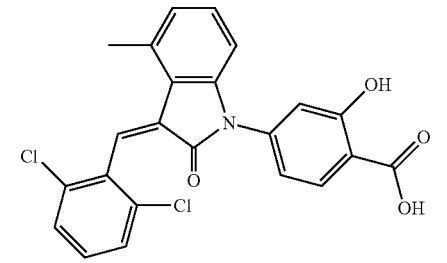
-continued
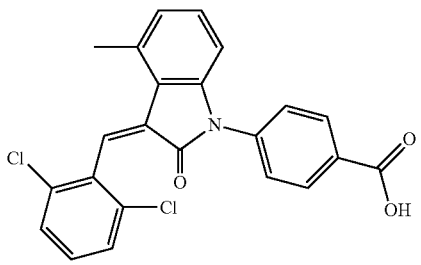
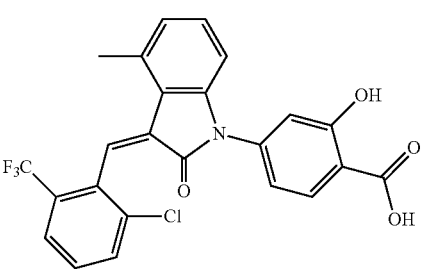
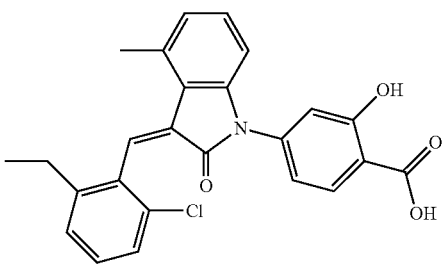
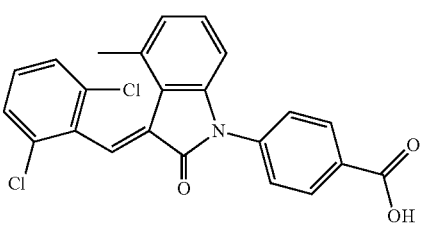
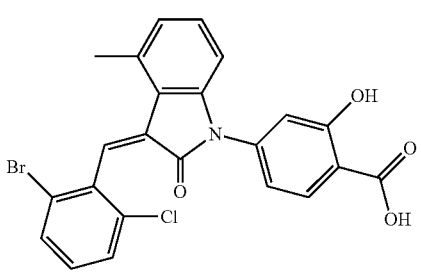
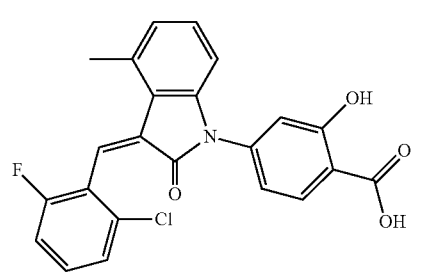

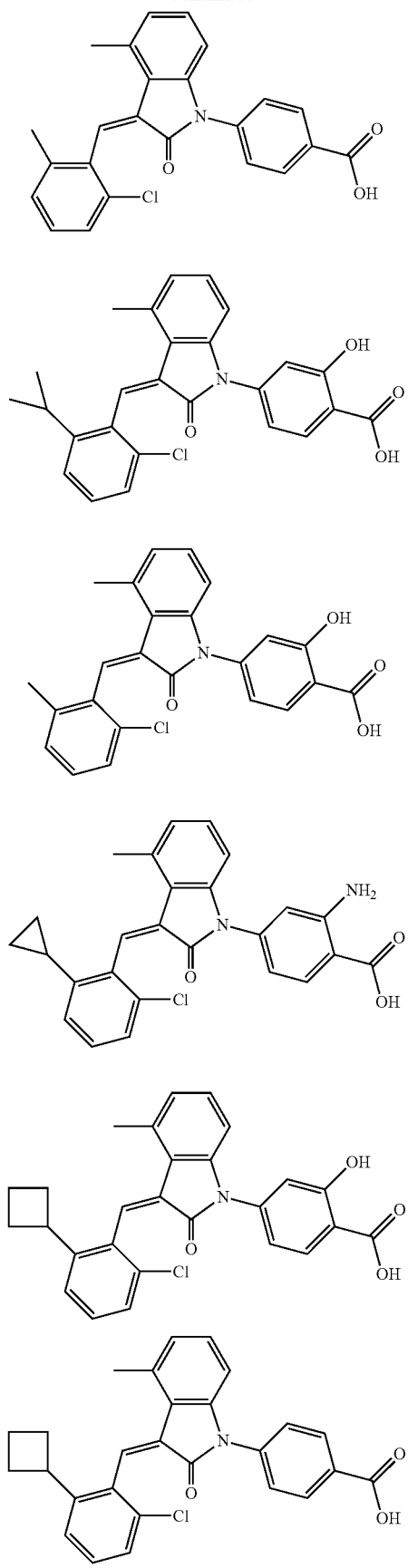
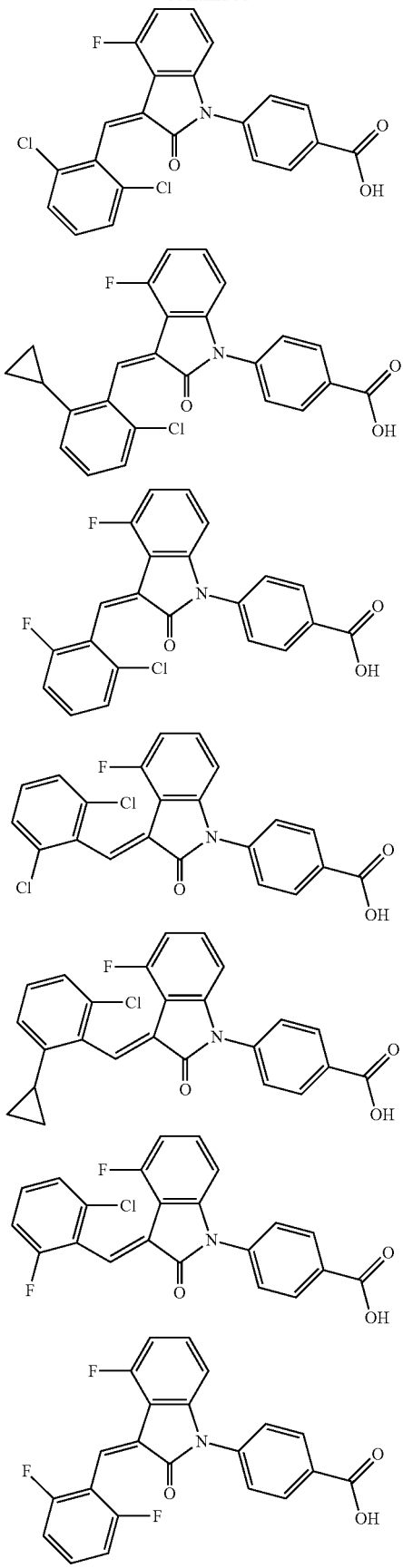

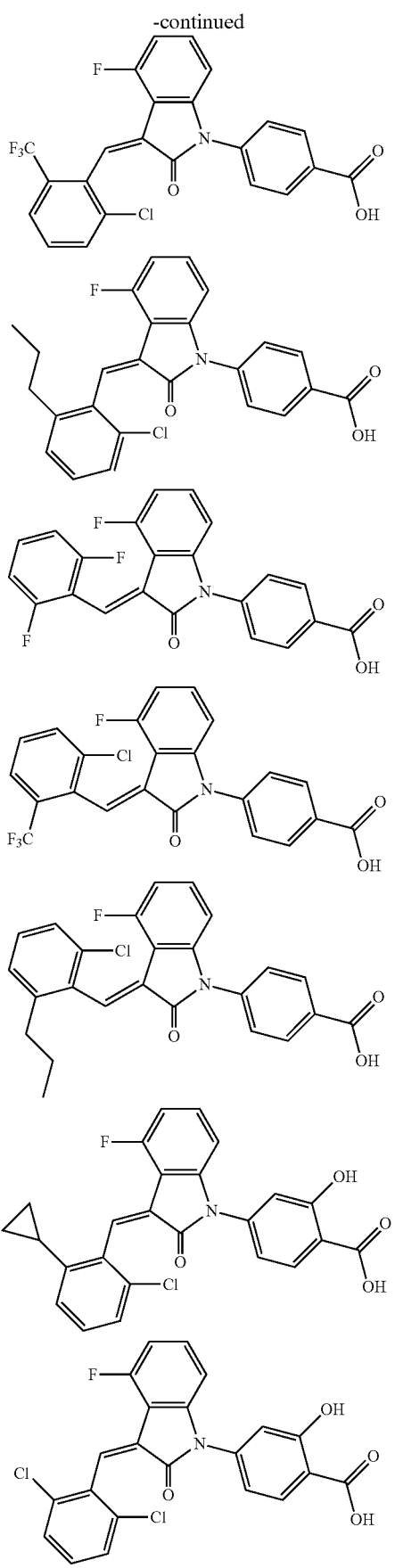
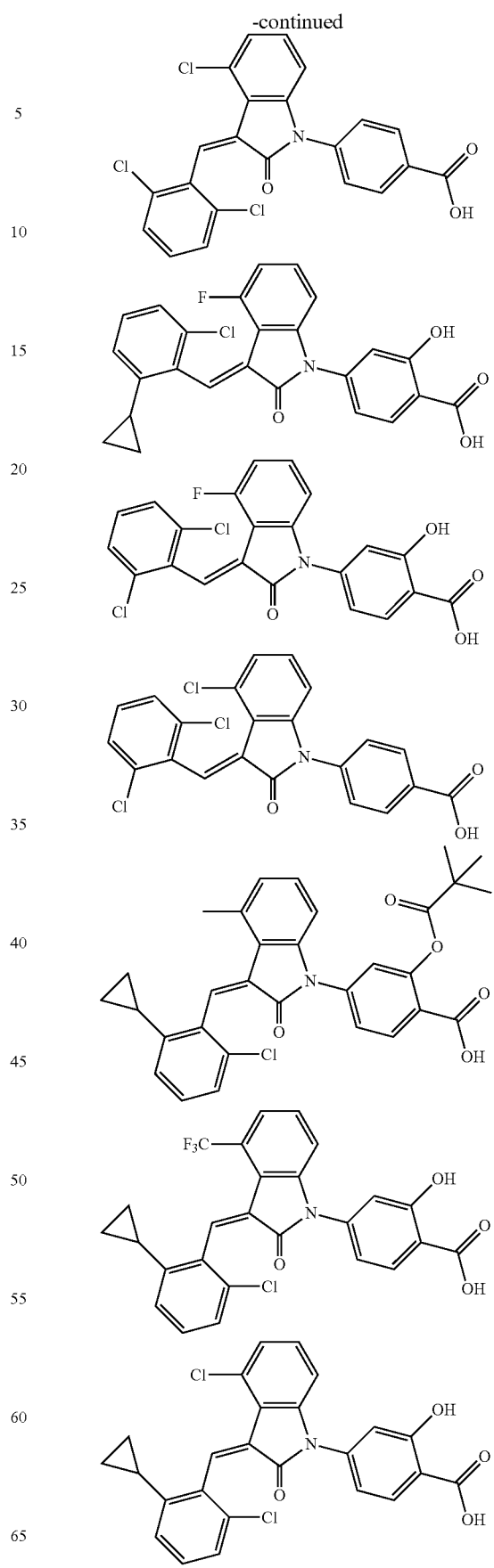

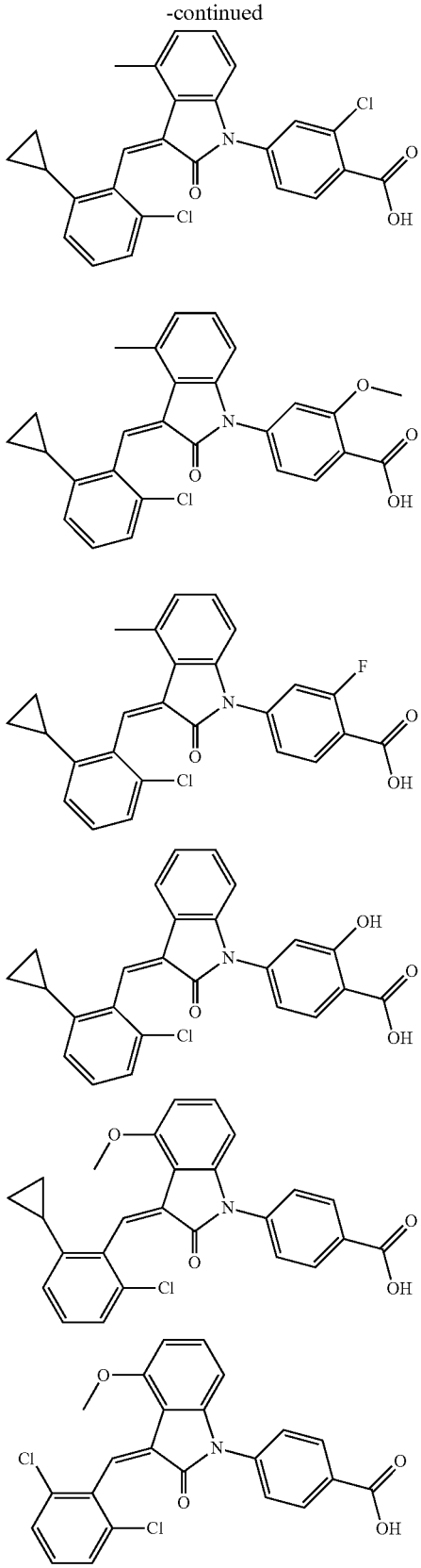

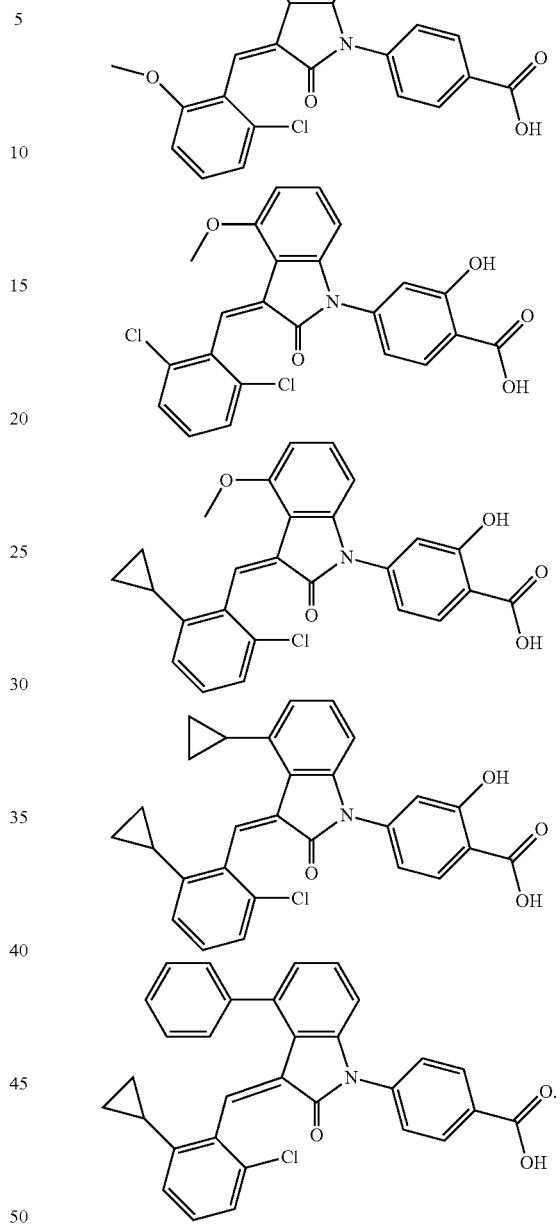

13. A pharmaceutical composition comprising the compound of claim 1, or a stereoisomer, a tautomer, a pharmaceutically acceptable salt, or a solvate thereof, and a pharmaceutically acceptable excipient.

14. The pharmaceutical composition of claim 13, further comprising one or more anti-inflammatory drugs selected from the group consisting of non-steroidal anti-inflammatory drugs, non-specific and specific cyclooxygenase-2 inhibitors, gold compounds, corticosteroids, tumor necrosis factor receptor antagonists, salicylate esters or salts, immunosuppressants and methotrexate.

* * * * *